US012737649B1

(12) United States Patent
Chi et al.

(10) Patent No.: US 12,737,649 B1
(45) Date of Patent: Sep. 15, 2026

(54) CONTINUOUS CONFIDENCE SCORING FOR A RULE-BASED NEGATION DETECTION SYSTEM

(71) Applicant: Amazon Technologies, Inc., Seattle, WA (US)

(72) Inventors: Wayne Chi, Santa Clara, CA (US); Travis Reed Goodwin, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 753 days.

(21) Appl. No.: 18/129,760

(22) Filed: Mar. 31, 2023

(51) Int. Cl.
*G06F 40/30* (2020.01)
*G06N 5/025* (2023.01)
*G16H 50/20* (2018.01)

(52) U.S. Cl.
CPC ............. *G06N 5/025* (2013.01); *G16H 50/20* (2018.01)

(58) Field of Classification Search
CPC ...... G06F 40/295; G06F 40/30; G06F 40/169; G16H 15/00
See application file for complete search history.

(56) References Cited

U.S. PATENT DOCUMENTS

| | | | | |
|---|---|---|---|---|
| 11,244,755 | B1 * | 2/2022 | Syeda-Mahmood | G16H 30/40 |
| 2018/0075012 | A1 * | 3/2018 | Allen | G16H 10/60 |
| 2020/0243175 | A1 * | 7/2020 | Katwala | G06F 40/169 |
| 2020/0250381 | A1 * | 8/2020 | Guo | G06F 40/289 |
| 2021/0020277 | A1 * | 1/2021 | Guo | G06F 16/335 |
| 2021/0334462 | A1 * | 10/2021 | Kukreja | G06F 40/295 |
| 2022/0343280 | A1 * | 10/2022 | Chan | G16H 40/20 |
| 2024/0062858 | A1 * | 2/2024 | Gnanasambandam | G16H 15/00 |
| 2025/0053739 | A1 * | 2/2025 | Yu | G16H 50/20 |

OTHER PUBLICATIONS

Chapman et al., "A Simple Algorithm for Identifying Negated Findings and Diseases in Discharge Summaries", Journal of Biomedical Informatics, vol. 34, 2001, pp. 301-310.

Devlin et al., "Bert: Pre-training of Deep Bidirectional Transformers for Language Understanding", arXiv:1810.04805v1, Oct. 11, 2018, 14 pages.

(Continued)

*Primary Examiner* — Daniel Abebe
(74) *Attorney, Agent, or Firm* — Nicholson DeVos Webster & Elliott LLP

(57) ABSTRACT

Approaches for determining continuous confidence scores for rule-based negation detection systems overcome deficiencies of existing rule-based negation detection systems that provide only binary output (e.g., negated or not negated). The approaches encompass a pointwise mutual information (PMI)-based approach in which PMI is measured between negation cue words and gold-standard negation annotations in a reference dataset. The approaches also encompass a conditional probability-based approach in which the condition probabilities that gold-standard negations exist in a reference dataset for negation cue words are measured. In both approaches, a form of association between negation cue words and gold-standard negations are measured to provide a more accurate indication of the rule-based system's confidence in a negation determination compared to a binary output.

20 Claims, 13 Drawing Sheets

(56) References Cited

OTHER PUBLICATIONS

Johnson, Mark, "How the Statistical Revolution Changes (Computational) Linguistics", Proceedings of the EACL 2009 Workshop on the Interaction between Linguistics and Computational Linguistics, Mar. 30, 2009, pp. 3-11.
Jurafsky et al., "Speech and Language Processing: An Introduction to Natural Language Processing, Computational Linguistics, and Speech Recognition", Computational Linguistics, vol. 26, No. 4, 2008, pp. 638-641.
Van Der Maaten et al., "Visualizing Data using t-SNE", Journal of Machine Learning Research, vol. 9, 2008, pp. 2579-2605.

* cited by examiner

```
{
"ENTITIES": [
    {
      "ID": 1,
      "BEGINOFFSET": 7,
      "ENDOFFSET": 22,
      "SCORE": 0.9998517036437988,
      "TEXT": "SODIUM CHLORIDE",
      "CATEGORY": "MEDICATION",
      "TYPE": "GENERIC_NAME",
      "TRAITS": [],
      "ATTRIBUTES": [
        {
          "TYPE": "ROUTE_OR_MODE",
          "SCORE": 0.32359644770622253,
          "RELATIONSHIPSCORE": 0.9719992280006409,
          "ID": 0,
          "BEGINOFFSET": 0,
          "ENDOFFSET": 6,
          "TEXT": "INFUSE",
          "TRAITS": []
        },
        {
          "TYPE": "STRENGTH",
          "SCORE": 0.9976715445518494,
          "RELATIONSHIPSCORE": 0.7892051339149475,
          "ID": 2,
          "BEGINOFFSET": 23,
          "ENDOFFSET": 27,
          "TEXT": "0.9%",
          "TRAITS": []
        },
        {
          "TYPE": "FORM",
          "SCORE": 0.9930835962295532,
          "RELATIONSHIPSCORE": 0.9956902861595154,
          "ID": 3,
          "BEGINOFFSET": 28,
          "ENDOFFSET": 36,
          "TEXT": "SOLUTION",
          "TRAITS": []
        },
...
        {
          "TYPE": "DURATION",
          "SCORE": 0.9392423033714294,
          "RELATIONSHIPSCORE": 0.9961885809898376,
          "ID": 8,
          "BEGINOFFSET": 91,
          "ENDOFFSET": 97,
          "TEXT": "3 DAYS",
          "TRAITS": []
        }
      ]
    }
  ],
...
}
```

ANNOTATED RESULT 306

FIG. 3

CLINICAL DATA 504

PT IS 40YO MOTHER, HIGH SCHOOL TEACHER. SLEEPING TROUBLE ON PRESENT DOSAGE OF CLONIDINE. RASH ON FACE AND LEG, SIGHTLY ITCHY. VYVANSE 50 MGS PO AT BREAKFAST DAILY, CLONIDINE 0.2 MGS – 1 AND 1 / 2 TABS PO QHS. BOGGY INFERIOR TURBINATES, NO OROPHARYNGEAL LESION.

ANNOTATED RESULT 506

| Entity ▼ | Type ▼ | Category ▼ | Traits |
|---|---|---|---|
| **40yo** 0.99+ score | ● Age | Protected health information | - |
| **Highschool teacher** 0.31 score | ● Profession | Protected health information | - |
| **Sleeping trouble** 0.82 score | ● Dx name | Medical condition | **Symptom** 0.67 score |
| **Clonidine** 0.99+ score | ● Generic name | Medication | - |
| **Rash** 0.99+ score | ● Dx name | Medical condition | **Symptom** 0.74 score |

FIG. 5

ANNOTATED RESULT
606

| Entity | Type | Category | Traits |
| --- | --- | --- | --- |
| **40yo**<br>0.99+ score | ● Age | Protected health information | - |
| **Highschool teacher**<br>0.31 score | ● Profession | Protected health information | - |
| **Sleeping trouble**<br>0.82 score | ● Dx name | Medical condition | **Symptom**<br>0.67 score |
| **Clonidine**<br>0.99+ score | ● Generic name | Medication | - |
| **Rash**<br>0.99+ score | ● Dx name | Medical condition | **Symptom**<br>0.74 score |
| **Oropharyngeal legion**<br>0.95 score | ● Dx name | Medical condition | Negation<br>0.99+ score |

FIG. 6

```
{
  "ENTITIES": [
    {
      "ID": 1,
      "BEGINOFFSET": 0,
      "ENDOFFSET": 20,
      "SCORE": 0.9980090260505676,
      "TEXT": "CERVICAL SPINAL CORD",
      "CATEGORY": "ANATOMY",
      "TYPE": "SYSTEM_ORGAN_SITE",
      "TRAITS": []
    },
    {
      "ID": 2,
      "BEGINOFFSET": 67,
      "ENDOFFSET": 73,
      "SCORE": 0.9989868998527527,
      "TEXT": "TRAUMA",
      "CATEGORY": "MEDICAL_CONDITION",
      "TYPE": "DX_NAME",
      "TRAITS": [
        {
          "NAME": "NEGATION",
          "SCORE": 0.798798680305481
        }
      ]
    }
  ],
  "UNMAPPEDATTRIBUTES": [],
  "MODELVERSION": "2.3.0"
}
```

ANNOTATED RESULT 1306

FIG. 13

CONTINUOUS CONFIDENCE SCORING FOR A RULE-BASED NEGATION DETECTION SYSTEM

BACKGROUND

The accuracy of negation detection in clinical documentation can affect how accurately a patient's medical history, symptoms, and conditions are understood. Negation detection in the clinical documentation context refers to the absence or non-existence of a particular medical condition, symptom, or sign. Consider an example where a patient has been diagnosed with lung cancer. The clinician will want to rule out smoking as the cause of the cancer. Accurately detecting the absence of smoking history in the patient's clinical documentation will be critically important to this. For example, there may be other potential causes of the cancer that the clinician should investigate. Negation detection can also be used to prevent errors in medical coding and billing as inaccurate negation detection can result in incorrect billing, leading to potential legal and financial consequences for clinicians and healthcare organizations.

Techniques described herein address these and other issues.

BRIEF DESCRIPTION OF DRAWINGS

Various examples in accordance with the present disclosure will be described with reference to the drawings, in which:

FIG. 3 illustrates an example of a human and machine-readable structured text representation of an annotated result produced by the pipeline, according to some embodiments of the invention.

FIG. 5 illustrates an example of a table representation of an annotated result produced by the pipeline, according to some embodiments of the invention.

FIG. 6 illustrates another example of a table representation of an annotated result produced by the pipeline, according to some embodiments of the invention.

FIG. 13 illustrates an example of a human and machine-readable structured text representation of the annotated result of FIG. 12 produced by the pipeline, according to some embodiments of the invention.

DETAILED DESCRIPTION

Figure 1:
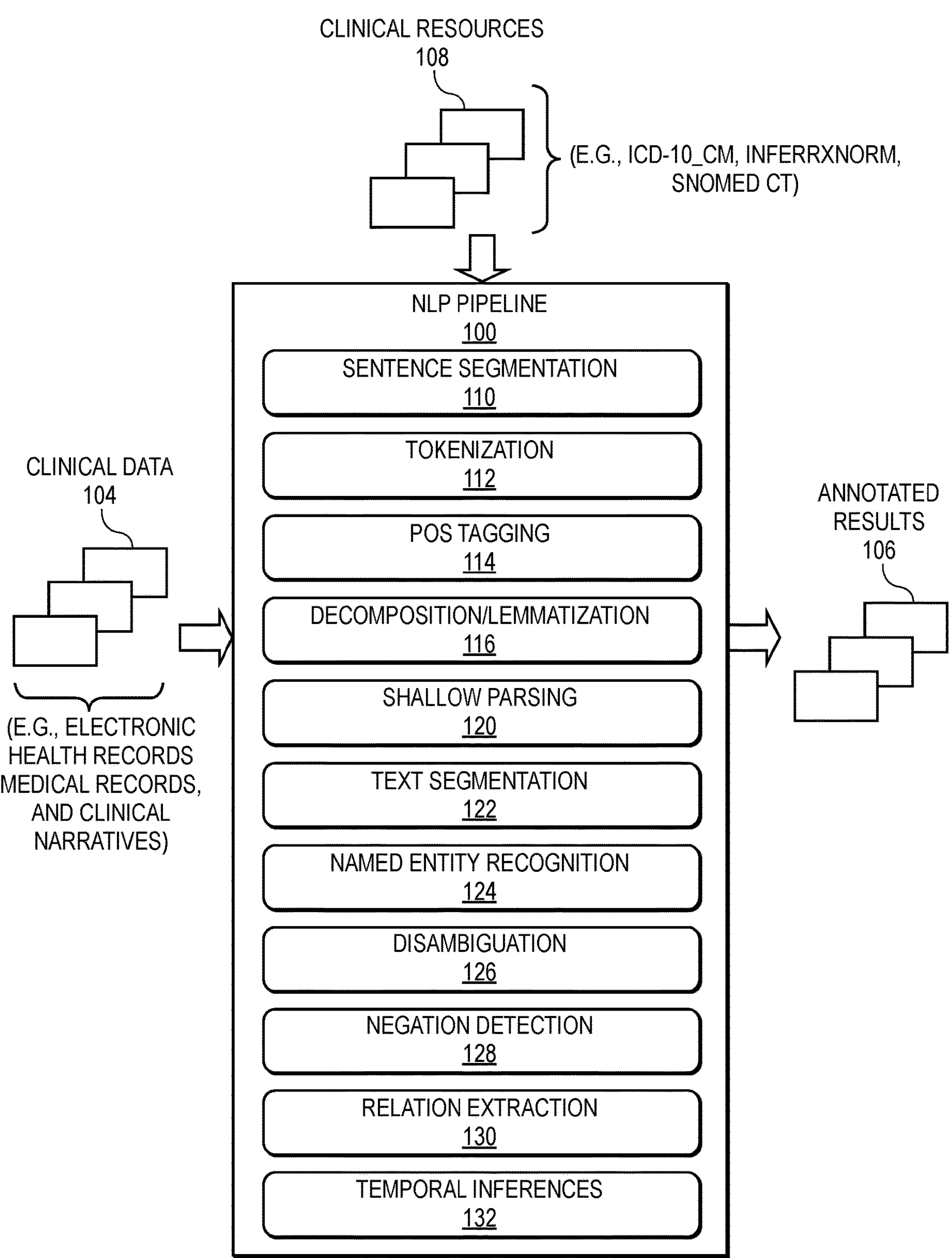
FIG. 1 illustrates example natural language processing pipeline, according to some embodiments of the invention.

The present disclosure relates to methods, systems, and non-transitory computer-readable media (collectively "techniques") for continuous confidence scoring for a rule-based negation detection system.

The accuracy of a computer system with respect to negation detection in natural language clinical documentation is vitally important to the success of the system. Early negation detection systems were rule-based. One example of a rule-based negation detection system works by using a set of predefined rules to identify negations in text. It does this based on the presence of certain negation cue words, such as "not," "never," "no," and "none." Once a candidate negation cue word is identified, the surrounding context is analyzed to determine whether the candidate negation cue word is being used as a negation. For example, if the system encounters the phrase "non smoker" in a sentence, it identifies "non" as a candidate negation cue word and then analyzes the word "smoker" to see if it should be negated. If the system determines that the word "smoker" is found to be modified by "non," then the system classifies the phrase "non smoker" as negated. The system also takes into account linguistic features such as the scope of the negation (e.g., the range of text that is affected by the negation). For example, in the phrase "patient says they do not have any symptoms," the scope of the negation is the entire phrase "have any symptoms," not just the word "symptoms."

Unfortunately, rule-based negation detection systems can produce false positives, especially when encountering semantic or grammatical ambiguity. In contrast, a machine learning-based negation detection system can better handle natural language ambiguities by learning to understand contextual information by statistical associations learned from a training dataset. Machine learning-based approaches typically use supervised learning techniques where a model is trained on a large, annotated dataset to learn patterns and features that can distinguish (classify) negated and non-negated instances. The model can be, for example, a classifier that is trained on a set of features extracted from clinical notes, such as part-of-speech tags, dependency relations, and word embeddings and that outputs a list of medical entities and their negation status. However, due to the supervised learning nature of machine learning-based approaches, a model that is trained based on a training dataset that is missing certain cues may not be able to learn sufficient statistical associations to identify negations associated with those missing cues.

The techniques herein combine the strengths of machine learning and rule-based approaches in a hybrid approach that encompasses a machine learning stage and a rule-based stage. In the machine learning stage, a trained model is used to determine negation of a given medical entity extracted from natural language text such as clinical documentation. If the trained model determines that the entity in context is negated, then the hybrid system determines that the entity is negated. However, if the trained model determines that the entity in context is not negated (affirmation), then the hybrid system passes the entity in context to a rule-based system to determine whether the entity in context is negated. If the rule-based system determines that the entity in context is negated, then the hybrid system determines that the entity is negated. On the other hand, if the rule-based system determines affirmation for the entity in context, then the hybrid system determines affirmation for the entity. By doing so, the techniques determine negation if and only if either the machine learning-stage or the rule-based stage determines negation. Otherwise, affirmation is determined.

Whether or not an entity is determined to be negated by the hybrid system, a user may appreciate knowing the confidence with which the system made the determination. The techniques encompass three different approaches for combining confidence scores from the machine learning-based approach and the rule-based approach. A first approach uses the average of the two scores of the confidence score for the entity, a second approach uses the larger of the two scores as the confidence score for the entity, and a third approach combines the two scores in a way that places higher emphasis on the larger confidence score.

Existing rule-based negation detection systems do not provide continuous confidence scores. Instead, they determine whether a given entity is or is not negated. Unfortunately, a binary output can be misleading to users as users may assume that all negation determinations are equally likely. The techniques herein provide two approaches for computing a continuous confidence score for a negation determination made by a rule-based system. In one approach, pointwise mutual information (PMI) is measured between negation cue words and gold-standard negation annotations in a dataset. In another approach, the conditional probabilities that gold-standard negations exist in a dataset for negation cue words are measured. In both approaches, a form of association between negation cue words and gold-standard negations are measured to provide a more accurate indication of the rule-based system's confidence in a negation determination compared to a binary output.

Example Natural Language Processing Pipeline

FIG. 1 illustrates example natural language processing (NLP) pipeline 100 in which the techniques for hybrid negation detection may be implemented. Pipeline 100 encompasses and is implemented by a set of NLP operations. The operations are performed by instructions executed by one or more computing devices. An example computing device is described below with respect to FIG. 11. For example, the instructions implementing the operations can be performed by one or more resource instances 1012 of provider network 1000 described below with respect to FIG. 10 where the one or more resource instances 1012 executed on one or more computing devices.

Overall, pipeline 100 takes clinical data 104 as input and produce annotated results 106 as output using clinical resources 108. The operations of pipeline 100 include sentence segmentation 110, tokenization 112, parts-of-speech (POS) tagging 114, decomposition/lemmatization 116, shallow parsing 120, text segmentation 122, named entity recognition 124, disambiguation 126, negation detection 128, relation extraction 130, and temporal inferences 132.

Clinical data 104 encompasses unstructured free text. For example, clinical data 104 can include text recorded in electronic health records (EHRs), medical records, and clinical notes and narratives. Pipeline 100 extracts information from clinical data 104 and produce annotated results 106. Annotated results 106 can be used by biomedical experts for research, used by clinicians for patient diagnoses and treatment, used for downstream processing by other computing applications such as clinical text mining applications, or used for other uses that are secondary to clinical diagnosis and treatment of patients.

Pipeline 100 processes clinical data 104 to gain various insights about its content. One type of examination that can be performed by pipeline 100 includes detection of entities. Entity detection involves pipeline 100 processing clinical data 104 to detect textual references to medical information such as medical conditions, treatments, test and test results, and medications. The entities detected by pipeline 100 in clinical data 104 can fall into various categories such as, for example, anatomy, medical condition, medication, Protected Health Information (PHI), and test treatment procedure.

For entity detection, pipeline 100 detects information from clinical data 104 in various classes including entities, attributes (a type of entity), types, and traits.

Entity: An entity is a textual reference to the name of relevant objects, such as people, treatments, medications, and medical conditions. For example, "Ibuprofen." Category: The generalized grouping to which a detected entity belongs. For example, "Ibuprofen" is part of the MEDICATION category. Type: The type of entity detected, which is scoped to a category. For example, "Ibuprofen" is in the GENERIC_NAME type in the MEDICATION category.

Attribute: An attribute is a detected entity providing information related to another detected entity, such as the dosage of a medication. For example, "200 mg" may be an attribute of the "Ibuprofen" entity. Since an attribute is an entity, "200 mg" is also an entity in addition to being an attribute of the "Ibuprofen" entity. Reference herein to "attribute" can be substituted with "entity" without loss of generality.

Trait: A trait is information that pipeline 100 determines about an entity, based on context. For example, a medication has the NEGATION trait if a patient is not taking it.

The existence in clinical data 104 of relevant entities detected by pipeline 100 are provided in annotated results 106. For example, annotated results 106 can be displayed in a graphical user interface in a graph form. The graphical user interface can be a type of interface that allows a user to interface with a computing device using graphical elements such as icons, graphics, buttons, windows, menus, or dialog boxes, arranged on a video display screen in a way that allows the user to navigate and interact with a software application in a visual and intuitive manner. The user may click on icons, select menu options, drag and drop files, and perform other actions using a pointing device (e.g., a mouse), a physical or virtual keyboard, or a touch sensitive surface such as a touch screen display. Additionally, or alternatively, annotated results 106 can be transmitted or stored in a human and machine-readable structured text data format such as in Java Script Object Notation (JSON), extensible Markup Language (XML), or the like.

Annotated results 106 include confidence scores for detected entities. A confidence score for an entity indicates the level of confidence that pipeline 100 has in the accuracy of the detection. For example, a confidence score can be a numerical value between 0 and 1 with 1 representing the highest confidence in the accuracy of the detection and 0 representing the lowest confidence in the accuracy of the detection.

Annotated results 106 can also include relationship scores for attributes. A relationship score indicates the level of confidence pipeline 100 has in the accuracy of the relationship between the attribute and its associated entity. For example, a relationship score can be a numerical value between 0 and 1 with 1 representing the highest confidence in the accuracy of the relationship between the two entities and 0 representing the lowest confidence in the accuracy of the relationship between the two entities.

A negated entity in annotated results 106 can also have a negation score that indicates the level of confidence pipeline 100 has in accuracy of the negation of the entity. For example, a negation score can be a numerical value between 0 and 1 with 1 representing the highest confidence in the accuracy of the negation and 0 representing the lowest confidence in the accuracy of the negation. Techniques are disclosed herein for detecting negated entities in clinical data 104 and for determining negation scores for negated entities that are included in annotated results 106.

Pipeline 100 is configured to detect and return useful information in unstructured clinical data 104 such as physician's notes, discharge summaries, test results, and case notes. Pipeline 100 is configured to implement natural language processing (NLP) models and operations to detect entities—textual references in clinical 104 to medical information such as medical conditions, medications, or protected health information (PHI).

Pipeline 100 supports a variety of downstream applications including patient case management and outcome, clinical research, medical billing and health care revenue cycle management, and ontology linking.

With respect to patient case management and outcome, pipeline 100 allows doctors and healthcare providers to manage and easily access medical information that does not fit into traditional forms. Pipeline 100 allows patients to report their health concerns in a narrative with more information than standard formats. By analyzing case notes, pipeline 100 allows health care providers to identify candidates for early screening of medical conditions before the condition becomes more difficult and expensive to treat.

With respect to clinical research, pipeline 100 allows life sciences and research organizations to optimize the matching process for enrolling patients into clinical trials. Pipeline 100 allows researchers to improve pharmacovigilance, perform post-market surveillance to monitor adverse drug events, and assess therapeutic effectiveness by easily detecting vital information in follow-up notes and other clinical texts. For example, pipeline 100 allows researchers to monitor how patients respond to certain therapies by analyzing their narratives.

With respect to medical billing and healthcare revenue cycle management, pipeline 100 allows payors to expand their analytics to include unstructured documents such as clinical notes. Pipeline 100 provides information about diagnoses for analysis that can be used to determine appropriate billing codes from clinical data 104. Pipeline 100 supports computer-assisted coding (CAC) and help to decrease time to revenue and improve reimbursement accuracy.

With respect to ontology linking, pipeline 100 detects entities from clinical data 104 and links those entities to standardized concepts and codes in clinical resources 108 such as, for example, the 2021 version of the International Classification of Diseases, 10th Revision, Clinical Modification (ICD-10-CM), INFERRXNORM, or the Systematized Nomenclature of Medicine, Clinical Terms (SNOMED CT).

Example Clinical Data and Annotated Results

Figure 2:
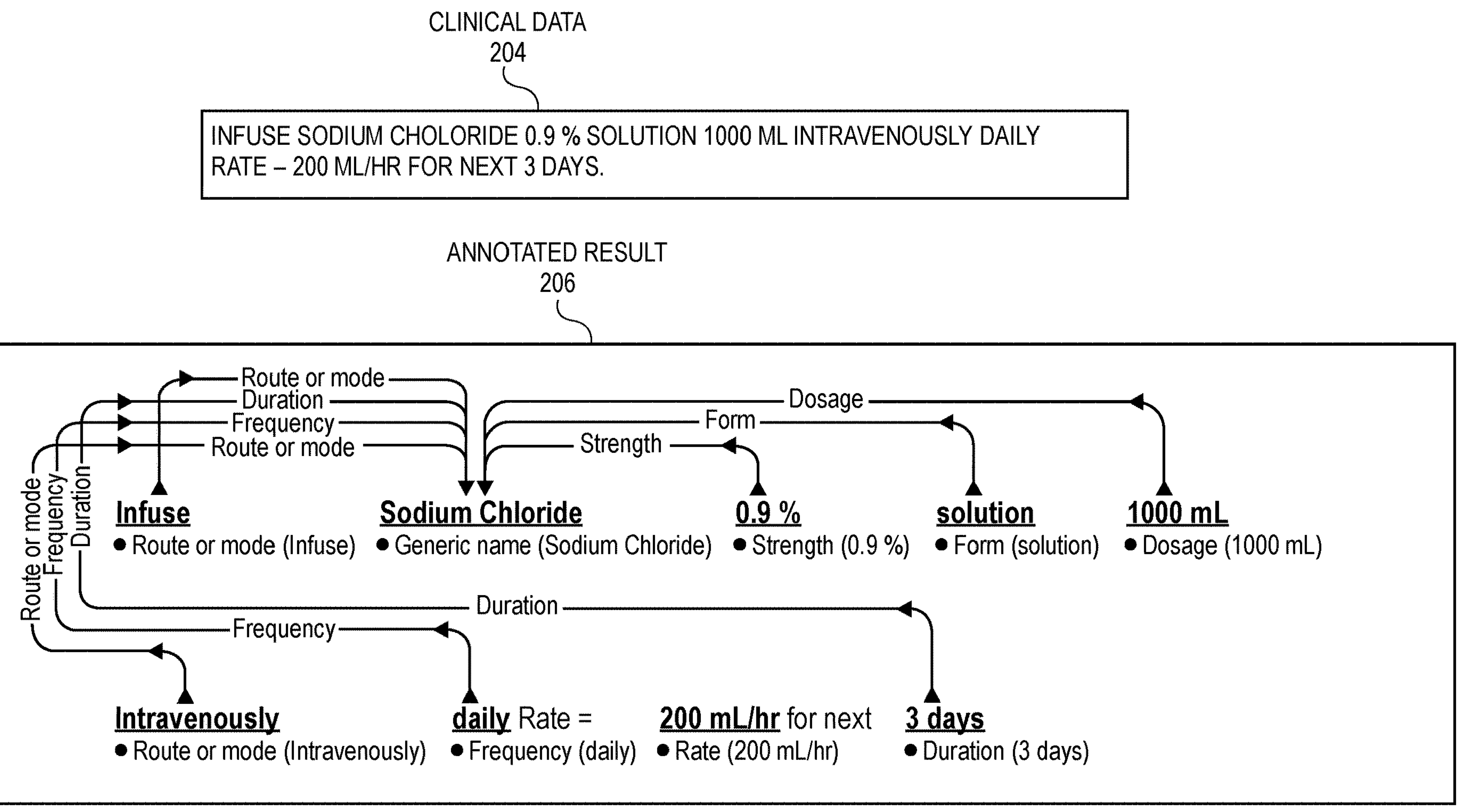
FIG. 2 illustrates an example of a graph representation of an annotated result produced by the pipeline, according to some embodiments of the invention.

FIG. 2 provides an example clinical data 204 and example annotated result 206 generated by pipeline 100 based on processing example clinical data 204. Clinical data 204 encompass unstructured free text. Annotated result 206, which may be displayed in a graphical user interface (GUI) such as in a web browser window, a mobile application GUI, or a desktop application GUI, provides a graph representation of clinical data 204.

In the example of FIG. 2, the text of clinical data 204 of "Sodium Chloride" is detected by pipeline 100 as an entity in the medication category of type "Generic name." Another possible type in the medication category could be "Brand name," for example. The text "Infuse" of clinical data 204 is detected by pipeline 100 as a "Route or mode" attribute of the "Sodium Chloride" entity that refers to the administration method of the medication. The text "0.9%" of clinical data 204 is detected by pipeline 100 as a "Strength" attribute of the "Sodium Chloride" entity that refers to the medication strength. The text "solution" of clinical data 204 is detected by pipeline 100 as a "form" attribute of the "Sodium Chloride" entity that refers to the form of the medication. The text "100 mL" of clinical data 204 is detected by pipeline 100 as a "dosage" attribute of the "Sodium Chloride" entity that refers to the amount of medication ordered. The text "intravenously" of clinical data 204 is detected by pipeline 100 as a "Route or mode" attribute of the "Sodium Chloride" entity that refers to the administration method of the medication. The text "daily" of clinical data 204 is detected by pipeline 100 as a "Frequency" attribute of the "Sodium Chloride" entity that refers to how often to administer the medication. The text "200 ml/hr" of clinical data 204 is detected by pipeline 100 as a "Rate" attribute of the "Sodium Chloride" entity that refers to the administration rate of the medication. The text "next 3 days" of clinical data 204 is detected by pipeline 100 as a "Duration" attribute of the "Sodium Chloride" entity that refers to how long the medication should be administered.

Annotated result 206 does not depict any confidence scores, relationship scores, or negation scores. However, annotated result 206 could include a confidence score determined by pipeline 100 in association with an entity that it is determined for. For example, a confidence score determined by pipeline 100 for an entity of annotated result 206 could be displayed in a graphical user interface upon detecting user input that selects one of the detected entities. Similarly, a graphical user interface could display a relationship score determined by pipeline 100 in association with a selected relationship it is determined for. In the example annotated result 206 there are no negated entities. However, for an annotated result that encompasses a negated entity, a graphical user interface could display a negation score determined by pipeline 100 in association with a selected negated entity that it is determined for where the negated entity is detected by pipeline 100 according to techniques disclosed herein and the negation score is determined by pipeline 100 according to techniques disclosed herein.

While an annotated result can be presented in a graphical user interface (GUI), an annotated result can be output by pipeline 100 in a human and machine-readable structured text representation such as in Java Script Object Notation (JSON), extensible Markup Language (XML), or the like. For example, FIG. 3 provides example annotated result 306 that is a JSON representation of a portion of annotated result 206. This example annotated result 306 provides confidence scores for the "Sodium Chloride" entity and confidence cores and relationship scores for various attributes of the "Sodium Chloride" entity.

Figure 4:
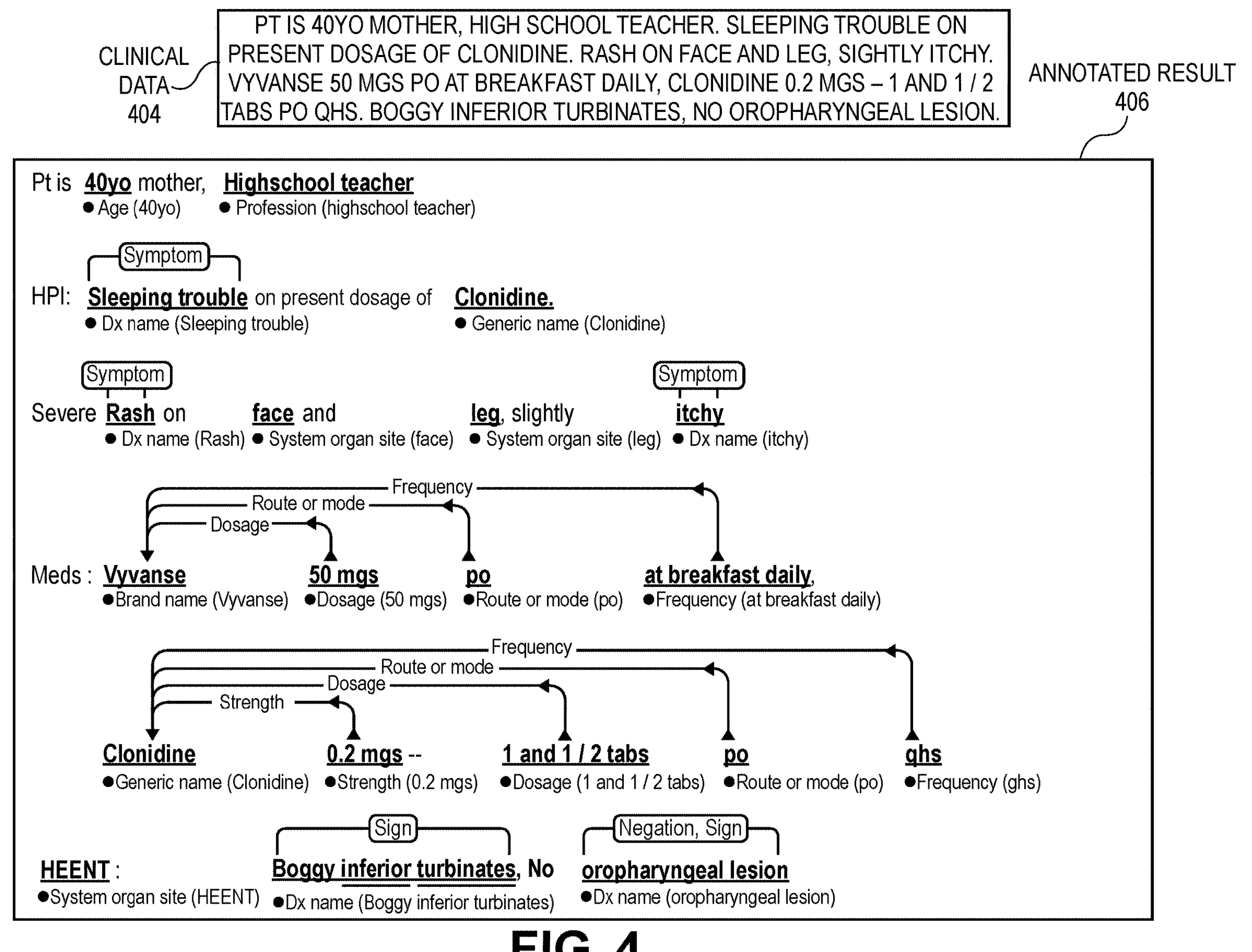
FIG. 4 illustrates another example of a graph representation of an annotated result produced by the pipeline, according to some embodiments of the invention.

An annotated result can include a negated entity. For example, FIG. 4 illustrates example annotated result 406 in a graph representation output by pipeline 100 after processing clinical data 404. In this example, the entity "oropharryngeal legion" is detected by pipeline 100 as type "Dx name." Pipeline 100 also determined that the entity is negated.

FIG. 5 illustrates another possible graphical user interface form for example annotated result 506 generated by pipeline 100 from clinical data 504. This form is a table form in which the various classes of information detected by pipeline 100 (entities, types, categories, and traits) correspond to columns of the table and each row corresponds to an entity detected by pipeline 100 in clinical data 504. The row also provides type information, category information, and trait information for the entity as detected by pipeline 100 from clinical data 504. Additionally, confidence scores determined by pipeline 100 for entities are listed in the Entity column and trait scores determined by pipeline 100 for traits are listed in the Traits column. One type of Trait that can be detected by pipeline 100 is negation. While the example of FIG. 5 does not include a negation trait, the negation score determined for a negation by pipeline 100 could be presented in a graphical user interface in the table form. For example, FIG. 6 illustrates example annotated result 606 which corresponding annotated result 506 of FIG. 5 but with an additional row for the "Oropharyngeal legion" that is determined by pipeline 100 to be negated. The Traits column of the row indicates that the entity is negated and provides the negation score determined by pipeline 100 for the entity.

Sentence segmentation 110 for clinical data 104 involves identifying and separating individual sentences within clinical data 104. Sentence segmentation 110 can be an important task in pipeline 100 because other operations of pipeline 100 may rely on accurate sentence segmentation to function properly. Sentence segmentation 110 may use a combination of heuristics and machine learning techniques. The heuristics can involve rules or patterns that are based on common features of language, such as punctuation, capitalization, and word order. For example, a common heuristic for sentence segmentation is to split the text into sentences wherever there is a period followed by a space and a capital letter. Machine learning techniques can involve training a model on a large dataset of annotated sentences to learn the patterns and structures of language that indicate the beginning and end of a sentence. This model can then be used to segment clinical data 104 into sentences based on the learned patterns. With clinical data 104, there may be challenges to accurate sentence segmentation due to the presence of medical terminology, abbreviations, and non-standard grammatical structures. Domain-specific knowledge and training data may be used when developing sentence segmentation models for clinical data 104.

Tokenization 112 for clinical data 104 involves breaking down the text of clinical data 104 into individual tokens, which are typically words or groups of words that convey a specific meaning. Tokenization 112 can be an important task in pipeline 100 because it allows clinical data 104 to be processed and analyzed at a more granular level. Tokenization 112 may involve a combination of heuristics and machine learning techniques. Heuristics involve rules or patterns that are based on common features of language, such as whitespace, punctuation, and capitalization. For example, a common heuristic for tokenization is to split the text into tokens wherever there is a whitespace character. Machine learning techniques involve training a model on a large dataset of annotated tokens to learn the patterns and structures of language that indicate the boundaries between tokens. This model can then be used to tokenize clinical data 104 based on the learned patterns. In clinical data 104, there may be additional challenges to accurate tokenization due to the presence of medical terminology, abbreviations, and non-standard grammatical structures. Tokenization 112 may use domain-specific knowledge and training data when developing tokenization models for clinical data 104. This may involve pre-processing clinical data 104 to handle challenges, such as expanding abbreviations and normalizing medical terms to a common format as defined in clinical resources 108.

Parts-of-speech (POS) tagging 114 for clinical data 104 involves identifying the grammatical structure of words in clinical data 104 by assigning a parts of speech labels to them. This can be an important task in pipeline 100 because it allows clinical data 104 to be analyzed at a more sophisticated level, such as identifying relationships between words, understanding the context of a sentence, and extracting meaningful information from clinical data 104. POS tagging 114 can be use a combination of heuristics and machine learning techniques. Heuristics involve rules or patterns that are based on common features of language, such as word endings, prefixes, and suffixes. For example, a common heuristic for POS tagging is to identify words that end in "ing" as verbs. Machine learning techniques involve training a model on a large dataset of annotated text to learn the patterns and structures of language that indicate the part of speech of each word. This model can then be used to assign POS labels to clinical data 104 based on the learned patterns. In clinical data 104, there may be additional challenges to accurate POS tagging due to the presence of medical terminology, abbreviations, and non-standard grammatical structures. Therefore, it is important to use domain-specific knowledge and training data when developing POS tagging models for clinical data 104. This may involve pre-processing clinical data 104 to handle challenges, such as normalizing medical terms to a common format and identifying special cases, such as negations or uncertain information.

Decomposition and lemmatization 116 are two related techniques involving normalizing clinical data 104 and extracting meaningful information from it. Decomposition and lemmatization 116 can be important for clinical data 104, where there may be a wide variety of medical terminology and abbreviations that need to be processed accurately. Decomposition involves breaking down complex medical terms and abbreviations into their constituent parts. This can involve expanding abbreviations and breaking down words into their component morphemes (the smallest meaningful units of language). For example, the medical term "CHF" (which stands for congestive heart failure) can be decomposed into the individual words "congestive," "heart," and "failure." Lemmatization involves reducing words to their base or root form (known as a lemma) to normalize the text and identify relationships between words. This can be useful for clinical data 104, where medical terms may have multiple forms (such as singular/plural, verb tense, or case) that need to be reconciled. For example, the word "diagnosed" might be lemmatized to its base form "diagnose." Both decomposition and lemmatization can be performed using a combination of heuristics and machine learning techniques. Heuristics involve rules or patterns that are based on common features of language or medical terminology, while machine learning techniques involve training a model on a large dataset of annotated text to learn the patterns and structures of language and medical terms. These techniques can be combined to accurately process and extract meaningful information from clinical data 104.

Shallow parsing 120 (equivalently "chunking") involves identifying and extracting specific phrases or chunks of text from clinical data 104. These chunks may include noun phrases, verb phrases, prepositional phrases, or other grammatical structures. Shallow parsing 120 involves breaking down the text into smaller chunks based on a set of predefined rules or patterns. These rules are typically based on the part of speech of each word in the text and the relationships between them. For example, a simple rule for identifying noun phrases might involve looking for consecutive words that are tagged as nouns. With clinical data 104, shallow parsing can be used to extract specific information of interest, such as medical conditions, treatments, or outcomes. This can be particularly useful for tasks such as information extraction, where specific pieces of information need to be extracted from clinical data 104. Shallow parsing can be performed using a variety of techniques, including rule-based systems, statistical models, or machine learning algorithms. These techniques can be trained on annotated datasets of clinical notes to learn the patterns and structures of language and medical terminology that indicate the presence of specific types of phrases or chunks. Once trained, the system can then be used to identify and extract these chunks from clinical data 104.

Text segmentation 122 for clinical data 104 involves dividing a larger text into smaller segments or sections based on some predefined criteria. This can be useful for organizing and structuring clinical data 104, which can be quite long and complex, into more manageable units for analysis. Various approaches can be used for text segmentation 122 including a combination of heuristics and machine learning techniques. Heuristics involve rules or patterns that are based on common features of language or medical terminology, while machine learning techniques involve training a model on a large dataset of annotated text to learn the patterns and structures of language and medical terminology that indicate the boundaries between different sections or segments of clinical data 104. With clinical data 104, text segmentation 122 may involve identifying different sections of clinical data 104 based on the type of information contained. For example, clinical data 104 might be segmented into sections for patient history, examination findings, laboratory results, diagnosis, and treatment plan. The criteria used for segmentation 122 may depend on the specific task or application and may involve different heuristics or machine learning models for different types of clinical data 104. Once clinical data 104 has been segmented, the individual segments can be analyzed separately or in relation to each other. This can facilitate of tasks of pipeline 100 such as summarization, information extraction, or topic modeling. Additionally, segmentation 122 can be performed to create a structured representation of clinical data 104, which can be more easily processed and analyzed by other operations of pipeline 100.

Named entity recognition (NER) 124 involves identifying and extracting specific named entities (such as medical conditions, treatments, drugs, and anatomical terms) from clinical data 104. NER in clinical data 104 can involve using a combination of rule-based systems and machine learning techniques to identify and label named entities. This involves training a machine learning model on a large dataset of annotated clinical notes, where each named entity has been manually labeled with its corresponding type (e.g., medical condition, treatment, drug). The model then uses statistical methods to identify patterns and relationships between words and phrases in the text and predict the most likely labels for each entity in clinical data 104. This can involve using contextual information such as the surrounding words, the part of speech of the word, and other linguistic features. One approach to NER in clinical notes is to use domain-specific knowledge to augment the model's performance. This may involve incorporating medical ontologies of clinical resources 108, such as the Unified Medical Language System (UMLS), to help identify medical terms and their relationships to other terms. Another approach is to use pre-trained language models that have been specifically trained on large datasets of medical text, such as the Medical Language Processing Ontology (MedLit) or the BioBERT model. Once the named entities have been identified and labeled, they can be further processed and analyzed using other operations of pipeline 100. This may involve tasks such as information extraction, relation extraction, or summarization, and can be used to support a range of clinical applications, such as clinical decision support or population health management.

Disambiguation 126 for clinical data 104 involves resolving the ambiguity of words or phrases that can have multiple meanings or interpretations in the medical domain. This can be an important task in pipeline 100 because ambiguity can lead to errors in downstream tasks, such as named entity recognition or information extraction. Several possible approaches can be used for disambiguation 126 of clinical data 104, including rule-based systems, statistical methods, and machine learning techniques. One possible approach involves using a combination of these methods to build a disambiguation model that can identify the most likely meaning of a given word or phrase in context. One possible method for disambiguation is word sense disambiguation (WSD), which involves identifying the correct meaning of a word based on the context in which it appears. This can be achieved using a variety of techniques, including supervised learning, unsupervised learning, and knowledge-based methods. For example, supervised learning methods can be trained on annotated datasets of clinical notes to learn the relationships between words and their contexts, while knowledge-based methods can use medical ontologies of clinical resource 108, such as the Unified Medical Language System (UMLS), to identify the most likely meaning of a given term based on its relationships to other terms in the ontology. Another possible method for disambiguation is entity linking, which involves identifying the correct entity that corresponds to a given mention in clinical data 104. This can involve using machine learning techniques to identify the most likely entity based on its relationships to other entities in the text and in external knowledge bases of clinical resource 108, such as UMLS or the National Library of Medicine's Medical Subject Headings (MeSH). Disambiguation 126 can be an important task in pipeline 100 because it can improve the accuracy and reliability of downstream tasks, such as information extraction and decision support. It can also enable the creation of more comprehensive and structured representations of clinical data 104, which can facilitate more advanced analysis and interpretation of clinical data 104.

Negation detection 128 involves identifying instances where a medical condition, treatment, symptom, or other entity of clinical data 104 is negated or negated in part. This can be an important task in pipeline 100 because negation can significantly affect the meaning of the text and can impact downstream tasks such as information extraction and decision making. Techniques disclosed herein for negation detection 128 use a hybrid approach that is a combination of a rule-based system and a machine learning-based system. A rule-based system can involve using a combination of lexical and syntactic patterns to identify negation cues, such as negation words like "not" or "no", as well as negation phrases like "without evidence of" or "rule out". These patterns can be used to identify negation cues in the text and to mark the corresponding medical concepts as negated. A machine learning approach can also be used to identify negation in clinical data 104. This can involves training a model on a large dataset of annotated clinical notes, where each instance of negation has been labeled. The model can learn to identify patterns and relationships between words and phrases in the text that indicate negation and can use this information to predict the likelihood of negation for instances of medical concepts in clinical data 104. Once negation has been detected, it can be used to modify the output of downstream tasks such as named entity recognition 124 or information extraction. For example, a negated medical concept may be treated differently than a non-negated concept when making a diagnosis or treatment plan. Negation detection 128 can be an important task of pipeline 100 because it can improve the accuracy and reliability of downstream tasks by ensuring that negated concepts are not misinterpreted or misrepresented.

Relation extraction 130 for clinical data 104 involves identifying the relationships between medical concepts mentioned in clinical data 104, such as a medication and a medical condition, or a procedure and an anatomical site. This can be an important task in pipeline 100 because it can enable the creation of structured representations of clinical data 104 that can be used for decision support, knowledge discovery, and quality improvement. There are several possible approaches to relation extraction 130 for clinical data 104, including rule-based systems, statistical methods, and machine learning techniques. One possible approach involves using machine learning techniques to train a model on a large dataset of annotated clinical notes, where each instance of a relationship between two medical concepts has been labeled. The model can learn to identify patterns and relationships between words and phrases in the text that indicate a particular type of relationship. Another possible approach to relation extraction 130 involves using medical knowledge bases of clinical resource 108, such as the Unified Medical Language System (UMLS), to identify relationships between medical concepts. These knowledge bases contain information about the relationships between medical concepts, such as the medications that are typically used to treat a particular medical condition or the procedures that are typically performed on a particular anatomical site. This information can be used to automatically identify relationships between medical concepts mentioned in clinical data 104. Once relationships have been identified, they can be used to create structured representations of clinical data 104, such as knowledge graphs or semantic networks. These representations can be used to support a variety of tasks, such as decision support, information retrieval, and clinical research. Relation extraction 130 can be an important task in pipeline 100 because it can enable the creation of more structured and comprehensive representations of clinical data 104. This can facilitate more advanced analysis and interpretation of clinical data 104, which can ultimately lead to better patient outcomes.

Temporal inference 132 for clinical data 104 involves identifying the temporal relationships between medical events mentioned in clinical data 104, such as diagnoses, treatments, and procedures. This can be an important task in pipeline 100 because it can enable the creation of timelines of clinical events, which can be used for decision support, quality improvement, and clinical research. There are several possible approaches to temporal inference 132 for clinical data 104, including rule-based systems, statistical methods, and machine learning techniques. One possible approach involves using a combination of lexical and syntactic patterns to identify temporal cues, such as temporal expressions like "last week" or "three months ago", as well as temporal relations like "before" or "after". These patterns can be used to identify the temporal relationships between medical events mentioned in clinical data 104. Another possible approach to temporal inference 132 involves using temporal knowledge bases of clinical resource 108, such as TimeML or HeidelTime, to identify temporal relationships between medical events mentioned in clinical data 104. These knowledge bases contain information about the temporal relationships between events, such as the time intervals between events or the order in which events occurred. This information can be used to automatically identify temporal relationships between medical events mentioned in clinical notes. Once temporal relationships have been identified, they can be used to create timelines of clinical events, which can be used for a variety of tasks, such as predicting the risk of future medical events, tracking the progress of a medical condition, or identifying the efficacy of a particular treatment. Temporal inference 132 can be an important task in pipeline 100 because it can enable the creation of more structured and comprehensive representations of clinical data 104. This can facilitate more advanced analysis and interpretation of clinical data 104, which can ultimately lead to better patient outcomes.

Example Hybrid Negation Detection Operation

Figure 7:
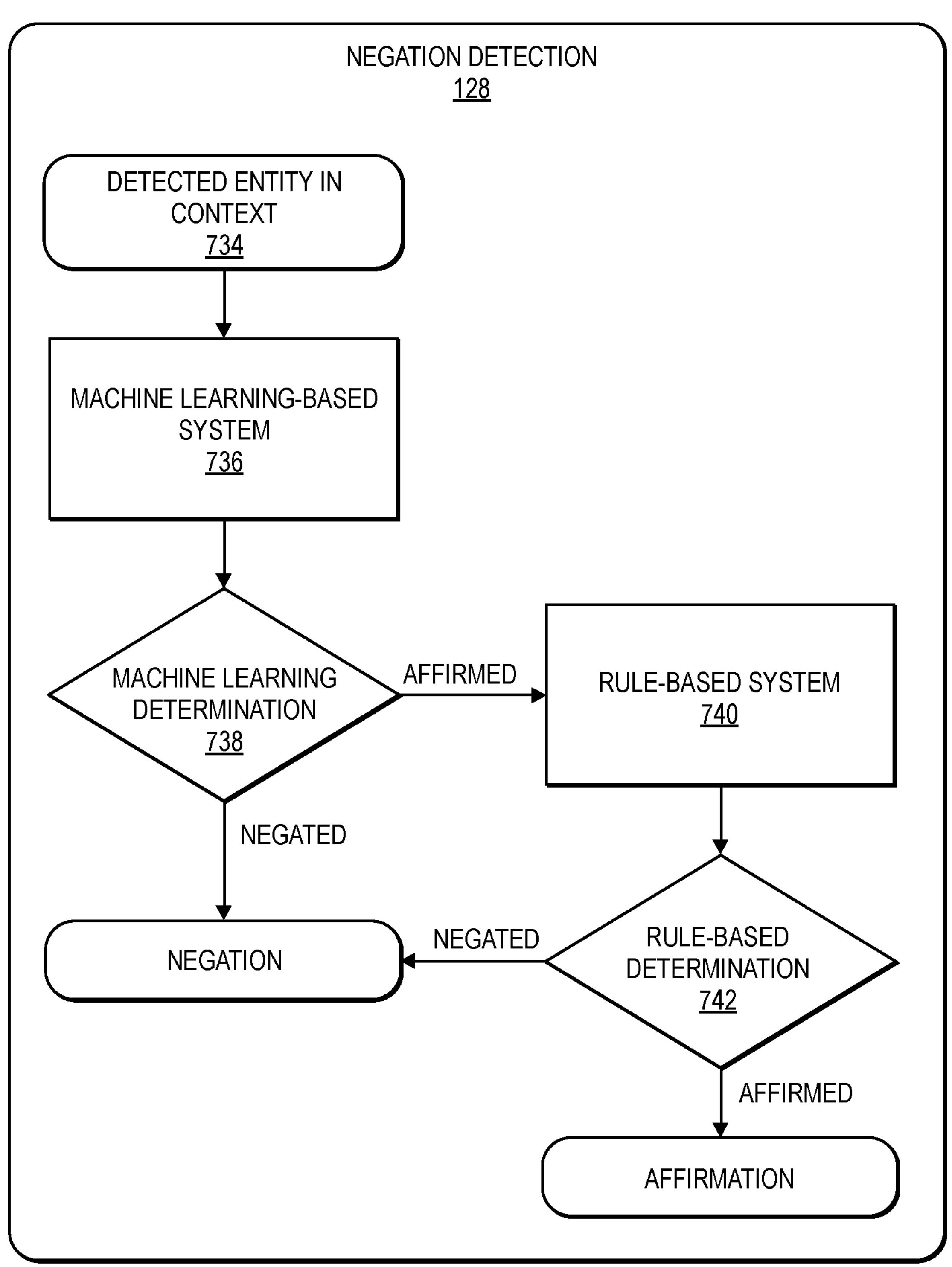
FIG. 7 illustrates an example of hybrid negation detection in the pipeline, according to some embodiments of the invention, according to some embodiments of the invention.

FIG. 7 illustrates an example of hybrid negation detection according to some embodiments of the invention. The operation is performed according to a hybrid negation detection approach that uses both a machine learning-based system and a rule-based system. Specifically, the approach determines that an entity detected in a clinical data context is negated if and only if either the machine learning-based system or the rule-based system determines the entity in the clinical data context is negated. If both systems determine that the entity in context is not negated, then the hybrid approach determines that the entity in context is not negated. If either or both systems determine that the entity in context is negated, then the approach determines that the entity in context is negated.

While the hybrid approach can result in increased false positives compared to an approach that determines negation if and only if both systems determine negation, the hybrid approach disclosed herein provides a technical benefit over other approaches. In particular, the machine learning-based system may not be trained to detect all possible negations that may occur in clinical data. Configuring the machine learning-based system to detect a novel negation requires retraining the model with examples of the new negation. In some cases, to avoid catastrophic loss, the model may need to be retrained from scratch with examples of all possible negations. Retraining the model involves a complex optimization process that consumes computing resources (e.g., CPU and GPU clock cycles) and electrical power. In contrast, adding a new rule to the rule-based system to detect the new negation does involve a complex optimization process and therefore consumes relatively fewer computing resources and electrical power than retraining. For example, adding a new rule may involve the system receiving and storing data in a database or other data structure representing a pattern matching expression (e.g., a regular expression) or other programmed negation detection logic (e.g., programmed if-then-else logic). Training a machine learning model for negation detection involves optimizing the parameters of the model based on a dataset of examples. This optimization process involves performed a larger number of calculations to minimize a cost function, which is computationally expensive compared to adding a new rule to a rule-based system.

The hybrid approach disclosed herein provides the technical benefits of both the machine learning-based negation detection system that can better handle natural language ambiguities by learning to understand contextual information by statistical associations learned from a training dataset and the rule-based negation detection system that can be more easily configured to detect a new negation that was not covered by the training dataset on which the machine learning-based system was trained. The hybrid system improves on prior hybrid systems by extending the time between trainings of the model, thereby conserving computing resources and electrical power.

The hybrid approach of FIG. 7 can be performed as part of negation detection in a natural language processing pipeline for clinical data. For example, the hybrid approach can be performed as part of negation detection 128 of pipeline 100 of FIG. 1.

According to the hybrid approach, negation detection 128 obtains an entity in a context 734 of clinical data 104. The entity is detected by named entity recognition 124 of pipeline 100. The detected entity can be a medical entity such as any of the following types or categories of medical entities. However, it should be understood that no particular entity or entities or type or types of entities are required by the disclosed techniques.

Anatomy: Example of an anatomy entity include a body system, an anatomic location, an anatomic region, a body site, a directional term (e.g., left, right, medial, lateral, upper, lower, posterior, anterior, distal, proximal, contralateral, bilateral, ipsilateral, dorsal, ventral, etc.)

Behavioral, environmental, and social health: Examples of a behavioral, environment, and social health entity include: a use status, frequency, amount, or duration of alcohol consumption; an allergy; a gender; a race; an ethnicity; a use status, frequency, amount, or duration of recreational drug use; or a use status, frequency, amount, or duration of tobacco use.

Medical Condition: Examples of a medical condition entity include: a present illness; a reason for visit; a medical history; determination of disease instance such as chronic, acute, sudden, persistent, or gradual; a directional term (see Anatomy above); an anatomical location.

Medication: Examples of a medication include: a brand name of a medication or therapeutic agent; and a non-band name, an ingredient name, or formula mixture of a medication or therapeutic agent.

Test, treatment, and procedure: Examples of a test, treatment, and procedure entity include: a procedure name, a test name, a treatment name, a test value, and a test unit.

Time expression: Examples of a time expression entity include: a date a medication was taken, a date a medical condition occurred, a date a test was performed, a date a procedure was performed, a date a treatment was administered.

The detected entity obtained at operation 734 is obtained in a context of clinical data 104 in which it was detected by named entity recognition 124. The context can be a sentence, a set of sentences, a paragraph, a clinical note, a clinical narrative, or other portion of clinical data 104 in which the entity was detected by named entity recognition 124. The entity in the context 734 obtained at operation 734 may or may not be negated by a negation cue. As used herein, a negation cue refers to a sequence of one or more words in clinical data that negates an entity detected in the clinical data. For example, the entity in the context might be negated if it is modified in the context by one of the following example negation cues: "no," "without," "no evidence," "without evidence," "negative for," "denies," "ruled out," "not," "resolved," "cannot," "rule out," etc. For example, the sentence "Patient is not suffering any headaches" could be obtained at operation 734 where "headache" is a detected entity and is negated by the negation cue "not." It should be understood, however, that the disclosed techniques are not limited to any particular negation cue or any particular set of negation cues.

After obtaining the entity in the context 734, negation detection 128 inputs the entity in the context 734 to machine learning-based negation detection system 736 to determine whether the entity in the context 734 is negated. Machine learning-based negation detection system 736 can determine whether the entity in the context 734 is negated in various different ways. No particular way is required. In general, however, machine learning system 736 may use a supervised or semi-supervised learning approach. Such an approach can involve collecting a labeled dataset composed of labeled contexts (e.g., sentences) where each sentence is labeled as positive or negative as to whether it contains a negation cue. The labeled dataset may be domain-specific such as one containing labeled examples particular to the medical or clinical domain. After collecting the dataset, relevant features are extracted from the labeled dataset. Such features may include words, phrases, or combinations of words (e.g., negation cues) that are indicative of negation. Once features are extracted from the labeled dataset, a machine learning model is trained based on the extracted features according to a machine learning algorithm to predict whether a given context contains a negation or not. Various different machine learning algorithms can be used including logistic regression, decision trees, support vector machines (SVMs), neural networks, conditional random fields (CRFs), Bidirectional Encoder Representations from Transformers (BERT), convolutional neural network (CNNs), Long Short-Term Memory Networks (LSTMSs), ensemble methods, etc. No particular machine learning algorithm is required, and the machine learning algorithm used can be selected according to the requirements of the particular implementation at hand including the size and the complexity of the labeled dataset and the computing resources available for training the model. Once the model is trained, its performance on a test dataset is evaluated using one or more metrics such as accuracy, precision, recall, or F1-score. If the performance on the test dataset is adequate, then the trained model can be used by system 736 to predict negation for new contexts such as the entity in the context 734.

An output of the machine learning-based negation detection system 736 for the entity in the context 734 is a score (numerical value) that represents either a probabilistic confidence that the entity in the context 734 is negated or a probabilistic confidence that the entity in the context 734 is not negated (affirmation). As used herein, a "score" refers generally to an assigned numerical value. For example, a score may be a continuous numerical value between 0 and 1 representing a probabilistic confidence of a negation determination where the continuous numerical value is represented in a computer as a floating-point value or a decimal value. If the score represents the probabilistic confidence that the entity in the context 734 is negated, then it may be referred to as a "negation" score. If the score represents the probabilistic confidence that the entity in the context 734 is not negated, then it may be referred to as an "affirmation" score. In either case, the score can be based on a maximum probability or a weighted sum of probabilities in a probability distribution of the machine learning model's output. The score can be a continuous numeric value between 0 and 1, for example. A threshold applied to the score can be used to determine whether the machine learning system 736 determined whether or not the entity in the context is negated. The threshold can be selected according to the requirements of the particular implementation at hand such as according to a precision-recall tradeoff. If the score is a negation score and is (at or) above the threshold, then the system 736 can be considered to have determined that the entity in the context 734 is negated. Otherwise, if the negation score is (at or) below the threshold, the system 736 can be considered to have determined that the entity in the context 734 is not negated. If the score is an affirmation score and is (at or) above the threshold, then the system 736 can be considered to have determined that the entity in the context 734 is not negated. Otherwise, if the affirmation score is (at or) below the threshold, the system 736 can be considered to have determined that the entity in the context 734 is negated.

At decision 738, negation detection 128 determines whether machine learning system 736 determined that the entity in the context 734 is negated or affirmed. If the system 736 determined the entity in the context 734 is negated, then negation detection 128 finally determines at decision 738 that the entity in context 734 is negated. In this case, negation detection 128 may still input the entity in the context 734 into rule-based system 740 for the purpose of determining a negation score for the entity in the context 734 as described in greater detail elsewhere herein.

On the other hand, if the machine learning system 736 determined at decision 738 that the entity in the context 734 is affirmed, negation detection 128 inputs the entity in the context 734 into rule-based system 740. If rule-based system 740 determines that the entity in the context 734 is negated, then negation detection 128 finally determines at decision 742 that the entity in the context 734 is negated. Otherwise, negation detection 128 finally determines at decision 742 that the entity in the context 734 is not negated (affirmed). Note that, in the hybrid approach, if the machine learning system 736 determines that the entity in the context 734 is not negated because it has not been trained on the particular negation cue used in the entity in the context 734 but the rule-based system 740 has a rule for detecting the particular negation cue in the entity in the context 734, then negation detection 128 will still finally determine at decision 742 that the entity in the context 734 is negated.

Rule-based system 740 can determine whether the entity in the context 734 is negated or not in various different ways. In one way, rule-based system 740 operates by defining a set of rules that identify the presence of negation cues in contexts (e.g., sentences). These rules are based on linguistic and syntactic patterns that are associated with negation in the clinical or medical domain. Rule-based system 740 can determine whether entity in the context 734 is negated by preprocessing the entity in the context 734. For example, rule-based system 740 may extract relevant features from the entity in the context 734 using tokenization 112 and decomposition or lemmatization 116 or other parsing or preprocessing. A set of one or more rules is then applied to the preprocessed text. A rule may be based on a linguistic and syntactic pattern associated with negation. For example, the linguistic and syntactic pattern may be defined according to a regular expression or according to programmed logic such as programmed if-then logic. Application of the set of rules may identify a negation cue in the entity in the context 734. Rule-based system 140 may then use syntactic patterns to determine the scope of the negation cue in the entity in the context 734. The output of the rule-based system 140 may include a list of any identified negation cues and their scopes. For example, the output may indicate whether the entity of the entity in the context 734 is within the scope of an identified negation cue.

Unlike machine learning-based system 736, rule-based system 740 may not output a continuous negation or affirmation score. For example, if a negation cue exists in the entity in the context 734, system 740 may simply output a binary or Boolean value indicating this. Additionally, or alternatively, if the entity of the entity in the context 734 is within the scope of an identified negation cue, then the rule-based system 740 may produce an output that identifies or contains the negation cue and a binary or Boolean value indicating that the entity is within the scope of the negation cue.

To address the binary nature of the output of rule-based system 740, two different techniques are provided for determining a continuous negation score for a negation detected by rule-based system 740. One or both of the techniques may be used in an implementation. If both, then the scores produced by the two techniques can be combined in some way, for example, as an average or weighted average. A first technique is based on pointwise mutual information (PMI) and is described below with respect to FIG. 8. A second technique is based on conditional probability and is described below with respect to FIG. 9.

A continuous negation score for a negation determined by rule-based system 740 improves the operation of pipeline 100. Pipeline 100 is improved because a better indication of the reliability of the system's 740 outputs compared to a binary indicator which treats all negation determinations as equally likely. Further, pipeline 100 is improved because the continuous negation score can be used to provide a better overall indication of a negation determination compared to a binary output.

Both the PMI-based approach and the conditional probability-based approach determine a negation score based on a measurement of association between: (A) a negation cue that is determined by rule-based system 740 to negate an entity in a context of clinical data, and (B) "gold-standard" negation cues in a reference set of clinical data. Like clinical data 104, the reference set of clinical data can encompass a text corpus of clinical notes, patient narratives, electrical health records, medical imaging reports, pathology reports, clinical trail data, medical literature, etc. The reference set of clinical data encompasses occurrences of a set of gold-standard negation cues that are determined to negate entities in context of the reference set of clinical data. Each such occurrence of a gold-standard negation cue in the reference set can be annotated or labeled as negating a respective entity in a respective context of the reference set. Note that it is possible for a negation cue to occur in the reference set without negating an entity. For example, a negation cue may negate an entity in one context but not in another context. A context of the reference set can be a phrase, a sentence, a paragraph, a clinical note, a clinical record, a clinical document, or other portion of the reference set of clinical data in which an entity of interest occurs. For example, an entity of interest can be word, or a sequence of words annotated or labeled as an entity for the purpose of training a machine learning model for a named entity recognition task.

Example PMI-Based Approach

Figure 8:
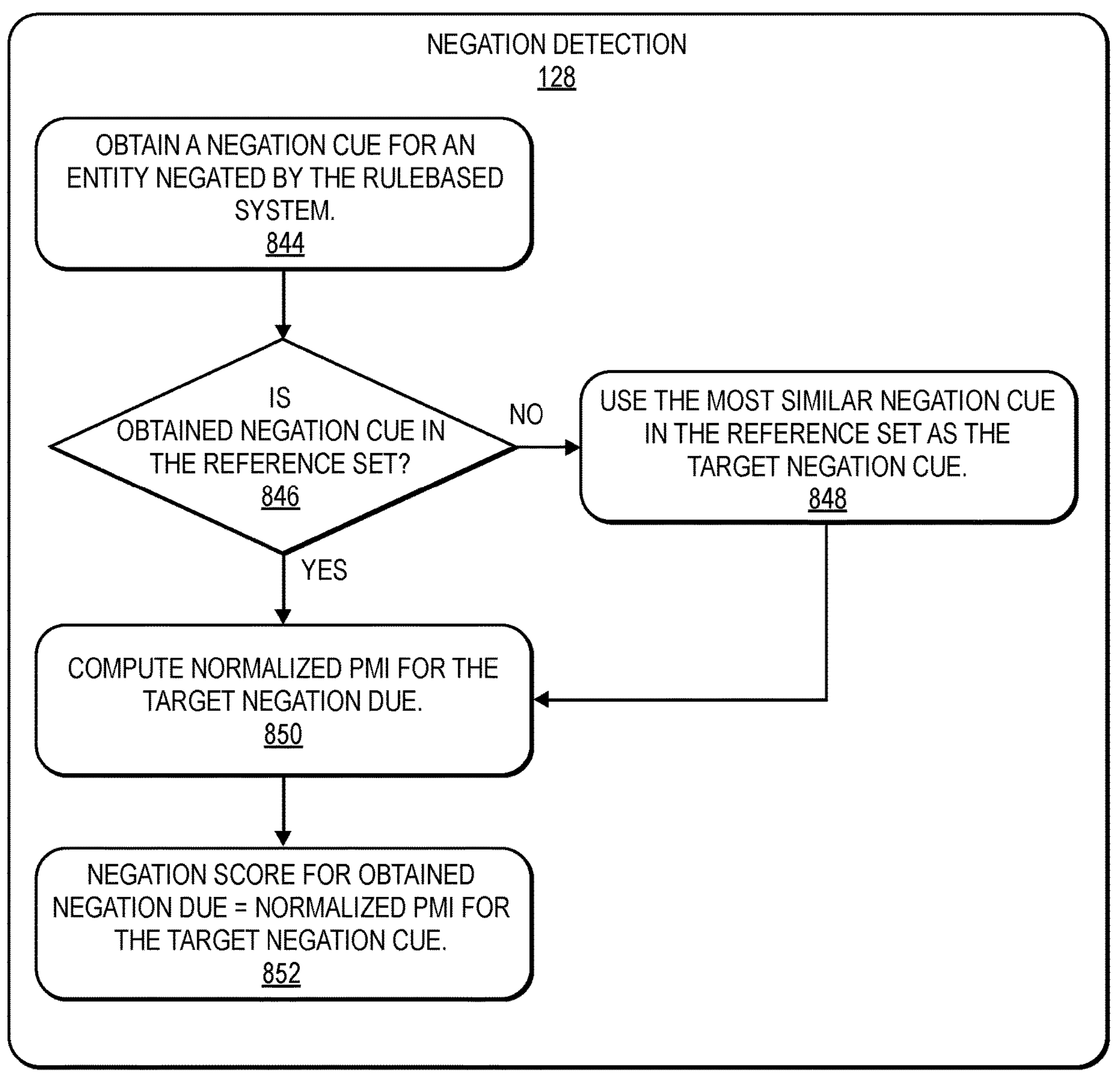
FIG. 8 illustrates an example pointwise mutual information-based approach for determining a continuous negation score for a negation determination by a rule-based system in the pipeline, according to some embodiments of the invention.

Turning first to FIG. 8, it illustrates a pointwise mutual information (PMI)-based approach for determining a negation score for a negation determination by rule-based system 740, according to some embodiments of the invention.

At operation 844, negation detection 128 obtains a negation cue for an entity determined to be negated in a context of clinical data by rule-based system 740. For example, the obtained negation cue can be a negation cue determined by rule-based system 740 to negate the entity of the entity in the context 734.

It is possible that the obtained negation cue determined by rule-based system 740 is not in the set of gold-standard negation cues included in the reference set of clinical data. For example, rule-based system 740 may be configured with a new rule to detect the obtained negation cue that is not in the set of gold-standard negation cues. For example, the set of gold-standard negation cues may have been used to train the machine learning model used by machine learning-based negation detection system 736 and the new rule may have added to rule-based system 740 after the model was trained. In the case where the obtained negation cue obtained at operation 844 is not in the set of gold-standard negation cues, negation detection 128 can determine the continuous negation score for the negation determination using the most similar gold-standard negation cue as the target negation cue. Accordingly, at decision 846, if the obtained negation cue determined by rule-based system 740 is not in the set of gold-standard negation cues, then, at operation 848, negation detection 128 determines the most similar gold-standard negation cue in the set of gold-standard negation cues and uses that most similar gold-standard negation cue as the target negation cue for the purpose of computing a continuous negation score for the negation determination. Otherwise, if the obtained negation cue is in the reference set of gold-standard negation cues, then the obtained negation cue can be used as the target negation cue.

The determination at operation 848 of the most similar gold-standard negation cue involves using high-dimensional vector representations of the obtained negation cue and the gold-standard negation cues. For example, the obtained negation cue and each of the gold-standard negation cues can be passed through a Bidirectional Encoder Representations from Transformers (BERT) model or the like (e.g., WORD2VEC, GOLVE, ELMO, UNIVERSAL SENTENCE ENCODER, DOC2VEC, etc.) to obtain an embedding for each. The embeddings are high-dimensional vectors provide latent-space representations of the semantic and syntactic features of the negation cues. The embeddings can be compared for similarity using a variety of distance metrics such as cosine similarity, Euclidean distance, or Manhattan distance. The embeddings for the gold-standard negation cues can be pre-generated prior to operation 848 and the embedding for the obtained negation cue generated as part of operation 848. The embedding generated for the obtained negation cue can be compared for similarity according to the distance metric to each of one or more embeddings generated for one or more gold-standard negation cues to determine the most similar gold-standard negation cue embedding according to the distance metric. The comparison for similarity can be efficiently facilitated by an appropriate data structure or algorithm such as a hash table, a K-d tree for nearest neighbor search, or approximate nearest neighbor search (e.g., ANNOY, FAISS, etc.). The gold-standard negation cue with the embedding that is most similar according to the distance metric to the embedding generated for the obtained negation cue can be selected as the target negation cue for the purpose of determining a continuous negation score for the negation determination.

At operation 850, the target negation cue is either: (A) the negation cue obtained at operation 844 from rule-based system 740 if the obtained negation cue is in the set of gold-standard negation cues from the reference set or (B) the gold-standard negation cue from the reference set that is most similar to the obtained negation cue obtained at operation 844 from rule-based system 740. At operation 850, negation detection 128 computes the normalized pointwise mutual information (PMI) for the negation determination. The following equation represents the normalized pointwise mutual information (PMI):

$$\text{NPMI\_norm}=(\text{NPMI}+1)/2$$

Here, NPMI is a value in the range of [−1, 1] which is mapped by the above-equation to the range [0, 1]. The following equation represents the calculation of NPMI:

$$\text{NPMI}(X,Y)=\text{PMI}(X,Y)/-\log 2(P(X,Y))$$

where $$\text{PMI}(X,Y)=\log(P(X,Y)/(P(X)*(P(Y)))$$

Here, the parameter P(X, Y) represents the probability of co-occurrence of the target negation cue and the gold-standard negation cues within the reference set of clinical data. For example, the parameter P(X, Y) can be determined by counting the number of contexts of the reference set in which the target negation cue and any of the gold-standard negation cues occur together and dividing that count by the total number of contexts of the reference set. The parameters P(X) and P(Y) represent the individual probabilities of the target negation cue and gold-standard negation cues within the reference set of clinical data, respectively. For example, the parameter P(X) can be determined by dividing the number of contexts in which the target negation cue occurs by the total number of contexts of the reference set. Similarly, the parameter P(Y) can be determined by dividing the number of contexts in which any of the gold-standard negation cues occur by the total number of contexts of the reference set. For the purposes of counting occurrences of the target negation cue in the reference set for the parameters P(X, Y), P(X), and P(Y) an occurrence of the target negation cue can be counted regardless if the occurrence is annotated or labeled as negating an entity in a context of the reference set. However, for purposes of counting occurrences of the gold-standard negation cues in the reference set for these parameters, an occurrence is counted only if the occurrence is annotated or labeled as negating a respective entity in a respective context of the reference set.

At operation 852, negation detection 128 determines the continuous negation score for the negation determination by rule-based system 140 as the normalized PMI determined at operation 850.

Example Conditional Probability-Based Approach

Figure 9:
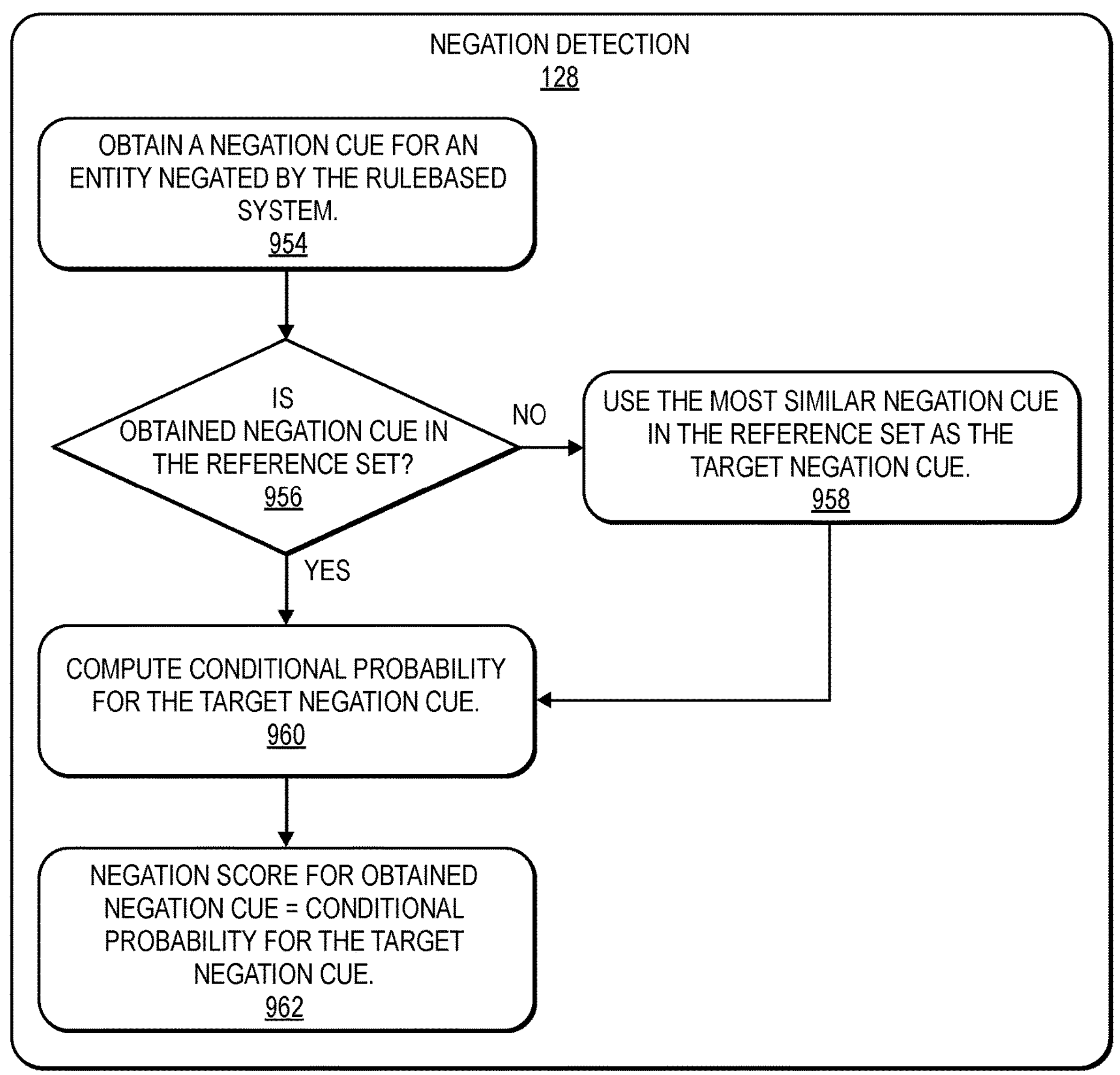
FIG. 9 illustrates an example conditional probability-based approach for determining a continuous negation for a negation determination by a rule-based system in the pipeline, according to some embodiments of the invention.

Turning next to FIG. 9, it illustrates a conditional probability-based approach for determining a negation for a negation determined by rule-based system 740, according to some embodiments of the invention.

The conditional probability-based approach is similar to the PMI-based approach except that a conditional probability is computed instead of a normalized PMI.

At operation 954, negation detection 128 obtains a negation cue for an entity determined to be negated in a context of clinical data by rule-based system 740. For example, the obtained negation cue can be a negation cue determined by rule-based system 740 to negate the entity of the entity in the context 734.

At decision 956, negation detection 128 determines whether the obtained negation cue is one of the gold-standard negation cues from the reference set of clinical data. If not, then negation detection 182 uses 958 the most similar gold-standard negation cue as the target negation cue as described above with respect to the PMI-based approach.

At operation 960, the target negation cue is either: (A) the obtained negation cue obtained at operation 954 from rule-based system 740 if the obtained negation cue is in the set of gold-standard negation cues from the reference set of clinical data or (B) the gold-standard negation cue from the reference set that is most similar to the obtained negation cue obtained at operation 954 from rule-based system 740. At operation 960, negation detection 128 computes the conditional probability of the existence of a gold-standard negation cue in the reference data set given the target negation cue. The following equation represents this conditional probability:

$$P(Y|X)=P(X,Y)/P(X)$$

In the above equation, the parameter P(X) represents a rate of occurrence of the target negation cue in the reference set of clinical data regardless of whether the occurrence is used as a negation in the reference set. The parameter P(Y) represents the rate of occurrence of all gold-standard negation cues in the reference set of clinical data. The parameter P(X, Y) represents a rate of occurrence of the target negation cue in the reference set when used as a negation in the reference set. In addition, to assist with low frequency values, additive or Laplacian smoothing can be used. For example, the parameter P(X) can be determined by counting the number of contexts of the reference set in which the target negation cue occurs regardless of whether the occurrence is annotated or labeled as negating an entity in the context and dividing that count by the total number of contexts of the reference set. The parameter P(Y) can be determined by counting the number of contexts of the reference set in which any gold-standard negation occurs and dividing that count by the total number of contexts of the reference set. The parameter P(X, Y) can be determined by counting the number of contexts of the reference set in which the target negation cue occurs where the target negation cue is annotated or labeled as negating an entity in the context and dividing that count by the total number of contexts of the reference set.

At operation 962, negation detection 128 determines the continuous negation score for the negation determination by rule-based system 140 as the conditional probability determined at operation 960.

Example Combined Negation Score

A continuous negation score determined according to the PMI-based approach or the conditional probability-based approach above can be used as the final negation score for a negation determination made by rule-based system 740. For example, the continuous negation score may be included in an annotated result in association with an entity determined by rule-based system 740 to be negated. Additionally, or alternatively, a continuous negation score determined for a negation determined by rule-based system 740 can be combined with a negation score determined by machine learning-based system 736. For example, the negation score determined by machine learning-based system 736 for the entity in the context 734 can be combined with the continuous negation score determined for the entity in the context 734 according to the PMI-based approach or the conditional probability-based approach. The combined negation score can be included in an annotated result in association with the entity determined to be negated.

The negation scores from the ML system 736 and the rule-based system 740 can be combined by taking an average of the negation scores. Alternatively, the negation scores can be combined by taking the maximum of the two scores. As yet another alternative, the negation scores can be asymmetrically combined such that the higher negation score has a greater impact on the combination than the lower negation score. For example, asymmetric combination may be based on the harmonic mean between the two scores. For example, the negation scores can be asymmetrically combined according to the following equation:

Combined negation score=1−HarmonicMean(NS-ML,NS-RULE)

In the above equation, the parameter NS-ML represents the negation score from machine learning system 736 for a negation determination for a particular entity in context and NS-RULE represents the negation score from the rule-based system 740 for a negation determination for the particular entity in context. The result of the combined negation score is an asymmetric aggregation of the negation scores from the machine learning system 736 and the rule-based system 740 where the higher the negation score, the greater impact it has on the aggregation.

Provider Network

Figure 10:
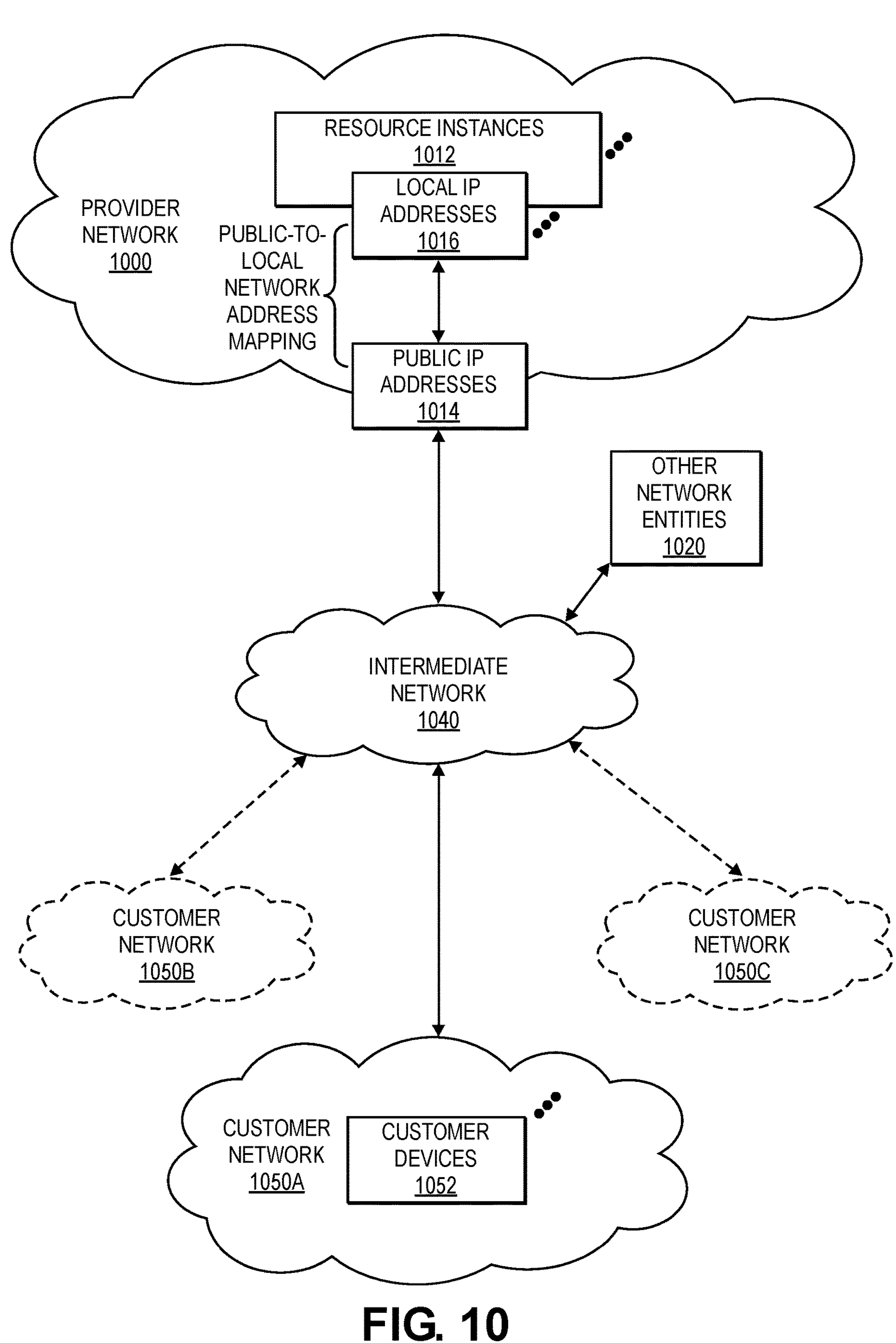
FIG. 10 illustrates an example provider network environment, according to some embodiments of the invention.

FIG. 10 illustrates provider network 1000. Provider network 1000 provides resources to customers via services that allow customers to purchase, rent, or otherwise obtain instances 1012 of resources, including but not limited to computing, networking, and data storage resources, implemented on electronic devices within provider network 1000 in one or more data centers.

Local Internet Protocol (IP) addresses 1016 are associated with resource instances 1012. Local IP addresses 1016 are the internal network addresses of resource instances 1012 in provider network 1000. Provider network 1000 also uses public IP addresses 1014. Provider network 1000 allows customers (e.g., customers that operates customer networks 1050A-1050C (or "client networks") including customer devices 1052) to dynamically associate public IP addresses 1014 provisioned to the customers with resource instances 1012 provisioned to the customers. Provider network 1000 also allows the customers to remap public IP address 1014 provisioned to the customers between resource instances 1012 provisioned to the customers.

Using resource instances 1012 and public IP addresses 1014, customers can implement customer-specific applications and offer them on intermediate network 1040, such as the Internet. Other network entities 1020 on intermediate network 1040 can then generate request traffic to public IP address 1014. The request traffic is routed from other network entities 1020 through intermediate network 1040 to provider network 1000. The request traffic received at provider network 1000 is routed to local IP addresses 1016 of resource instances 1012 which process (handle) the request traffic. Response traffic generated by resource instances 1012 is routed onto intermediate network 1040 back to other network entities 1020.

Local IP addresses 1016 are internal or private network addresses of resource instances 1012. For example, local IP addresses 1016 can be within address blocks reserved by Internet Engineering Task Force (IETF) Request for Comments (RFC) 1918 or of an address format specified by IETF RFC 4193 and can be mutable within provider network 1010. Network traffic originating outside provider network 1010 is not directly routed to local IP addresses 1016. Instead, the traffic uses public IP addresses 1014 that are mapped to local IP addresses 1016. Provider network 1000 can include networking devices or appliances that provide network address translation (NAT) or similar functionality to perform the mapping between public IP addresses 1014 and local IP addresses 1016.

Provider network 1000 can provide its capabilities to customers according to one or more of a variety of different service models including Software-as-a-Service (SaaS), Platform-as-a-Service (PaaS), Infrastructure-as-a-Service (IaaS), or any other provider network service model.

With SaaS, a capability is provided to customers using software applications of provider network 1000 and running on the infrastructure of the provider network 1000. The applications may be accessible from various remote electronic devices through either a thin client interface such as a command line interface (CLI), a graphical user interface (GUI) (e.g., via a web browser or a mobile or web application), a Software Development Kit (SDK), or any other interface. The infrastructure of provider network 1000 includes the hardware resources such as server, storage, and network resources and software deployed on the hardware infrastructure that support the services being provided. Typically, under the SaaS model, customers do not manage or control the underlying infrastructure including network, servers, operating systems, storage, or individual application capabilities, except for limited customer-specific application configuration settings.

With PaaS, customers are provided the capability to deploy, onto hardware and software infrastructure of provider network 1000, customer-created or acquired applications using programming languages, libraries, services, and tools supported by provider network 1000 or other sources. Typically, under the PaaS model, customers do not manage or control the underlying hardware and software infrastructure including network, servers, operating systems, or storage, but can have control over the deployed applications and possibly configuration settings for the application-hosting environment.

With IaaS, customers are provided the capability to provision processing, storage, networks, and other fundamental computing resources where the customers can deploy and run arbitrary software, which can include operating systems and applications. The customers typically do not manage or control the underlying hardware and software infrastructure but can have control over operating systems, storage, and deployed applications and possibly limited control of selecting network components such as, for example, host firewalls.

Provider network 1000 can provide its capabilities to customers according to one or more of a variety of different deployment models including as a private cloud, as a community cloud, as a public cloud, as a hybrid cloud, or any other provider network deployment model.

In a private cloud, the hardware and software infrastructure of provider network 1000 is provisioned for exclusive use by a single organization which can comprise multiple customers. The private cloud is owned, managed, and operated by the organization, a third party, or some combination of them, and it can exist on or off premises.

In a community cloud, the hardware and software infrastructure of provider network 1000 is provisioned for exclusive use by a specific community of customers from organizations that have shared concerns such as mission security requirements, policy, and compliance considerations. The community cloud is owned, managed, and operated by one or more of the organizations in the community, a third party, or some combination of them, and it can exist on or off premises.

In a public cloud, the infrastructure is provisioned for open use by the public. The public cloud is owned, managed, and operated by a business, academic, or government organization, or some combination of them. A public cloud can exist on the premises of the public cloud provider.

In a hybrid cloud, the infrastructure is a composition of two or more distinct cloud infrastructures (private, community, public, or any other cloud infrastructure) that remain unique entities, but that are bound together by standardized or proprietary technology that enables data and application portability such as, for example, cloud bursting for load balancing between clouds.

Computer System

Figure 11:
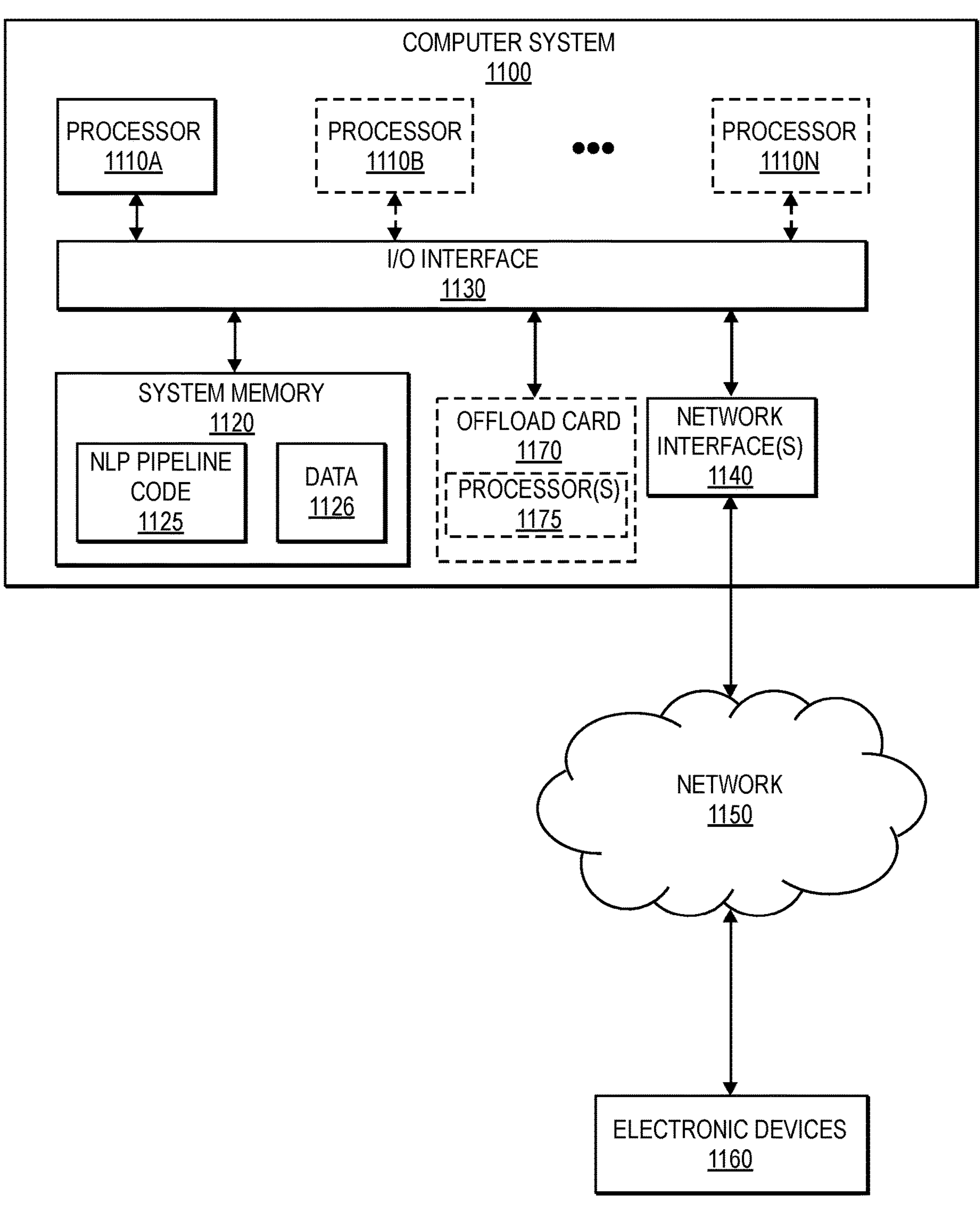
FIG. 11 is a block diagram illustrating an example computer system, according to some embodiments of the invention.
Figure 12:
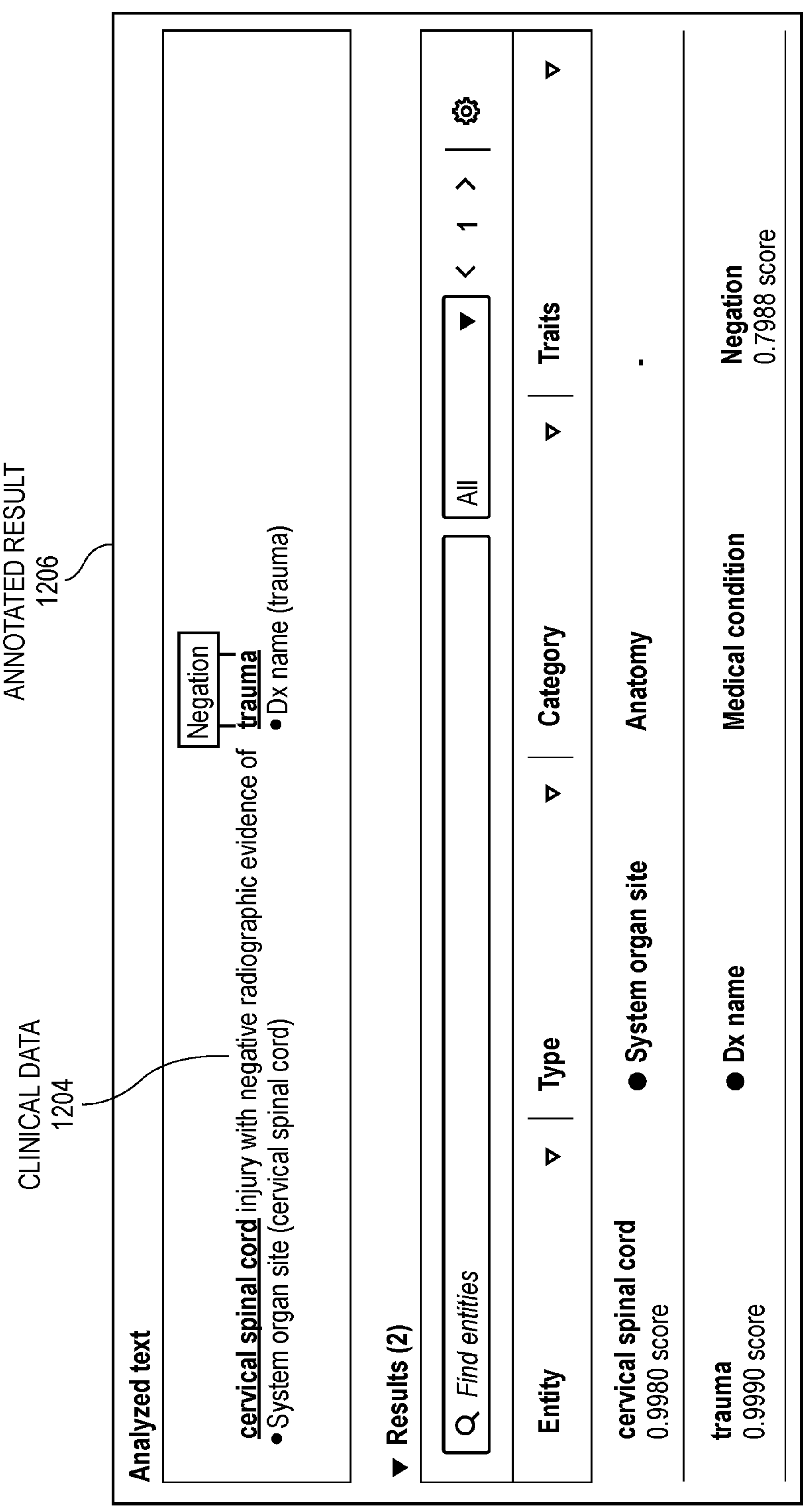
FIG. 12 illustrates an example of an annotated result produced by the pipeline, according to some embodiments of the invention.

A system that implements a portion or all the techniques described herein can include a general-purpose computer system (also referred to herein as a "computing device"). FIG. 11 illustrates computer system 1100. Computer system 1100 includes one or more processors 1110A-N coupled to system memory 1120 via input/output (I/O) interface 1130. Computer system 1100 further includes network interface 1140 coupled to I/O interface 1130. While computer system 1100 can be a single computing device, computer system 1100 can encompass one computing device, or any number of computing devices configured to work together as a single computer system.

Computer system 1100 can be a uniprocessor system including one processor 1110, or a multiprocessor system including several processors 1110A-N (e.g., two, four, eight, or another suitable number). Each processor 1110A-N can be any suitable hardware processor capable of executing instructions and its functionality implemented at least in part by integrated circuitry composed of semiconductor material (e.g., silicon), but its functionality can additionally be implemented by software (e.g., firmware). For example, each processor 1110A-N can be general-purpose or embedded microprocessor implementing an instruction set architecture (ISAs) such as x86, ARM, POWERPC, SPARC, or MIPS.

System memory 1120 stores instructions and data accessible by processor(s) 1110. Program instructions and data implementing one or more desired functions, such as those methods, techniques, and data described above, are shown stored within the system memory 1120 as natural language processing (NLP) pipeline code 1125 (e.g., executable to implement, in whole or in part, the NLP pipeline 100) and data 1126.

System memory 1120 is a non-transitory computer-readable medium such as, for example, a volatile or a non-volatile computer-readable medium. Non-limiting examples of electronic devices that encompass volatile computer-readable media include random-access memory (RAM) devices and cache memory devices. For example, system memory 1120 may be implemented at least in part by dynamic random-access memory (DRAM) devices or static random-access memory (SRAM) devices. Non-limiting examples of electronic devices that encompass non-volatile computer-readable media include read-only memory (ROM) devices, hard disk drives, solid-state drives, flash drives, magnetic tape drives, optical disk drives, and other types of memory cards. For example, system memory 1120 may be implemented at least in part by any or all of: flash memory devices, magnetic disk storage devices, optical disk storage devices, phase-change memory (PCM) devices, ferroelectric RAM (FRAM) devices, magnetoresistive RAM (MRAM) devices, resistive RAM (RRAM) devices, mask ROM devices, programmable ROM (PROM) devices, erasable programming ROM (EPROM) devices, or electrically erasable programmable ROM (EEPROM) devices. Non-transitory computer-readable media is distinct from, but may be used in conjunction with, transitory electronic signals, electromagnetic carrier waves, and other transitory signals.

I/O interface 1130 is configured to coordinate I/O traffic between processor(s) 1110, system memory 1120, and any peripheral devices, including network interface 1140. I/O interface 1130 performs protocol, timing, or other data transformations to convert data signals from one component (e.g., system memory 1120) into a format suitable for use by another component (e.g., processor(s) 1110). I/O interface 1130 can include support for devices attached through various types of peripheral buses such as, for example, a Peripheral Component Interconnect (PCI) bus, a QUICKPATH INTERCONNECT (QPI) bus, a UltraPath Interconnect (UPI) bus, a UNIVERSAL SERIAL BUS (USB), or other suitable bus. A function of I/O interface 1130 can be split into two or more separate components such as, for example, a north bridge and a south bridge. Some or all the functionality of I/O interface 1130 such as, for example, an interface to system memory 1120, can be incorporated directly into processor(s) 1110.

Network interface 1140 allows data to be exchanged between computer system 1100 and electronic devices 1160 attached to network 1150. Network interface 1140 supports communication via any suitable wired or wireless data networks such as, for example, a wired or wireless Ethernet networks. Additionally or alternatively, network interface 1140 supports communication via telecommunications or telephony networks, such as analog voice networks or digital fiber communications networks, via storage area networks (SANs), such as Fibre Channel SANs, or via any other suitable type of network or protocol.

Computer system 1100 optionally includes offload card 1170. Offload card 1170 includes one or more processors 1175 and possibly includes network interfaces 1140. Offload card 1170 is connected to I/O interface 1130. For example, computer system 1100 can act as a host for compute instances such as, for example, virtual machine instances or container instances. In this case, processor(s) 1175 of offload card 1170 can execute a virtualization manager that manages compute instances that execute on processor(s) 1110. The virtualization manager can perform compute instance management operations such as, for example, pausing or unpausing compute instances, launching or terminating compute instances, performing memory transfer/copying operations, etc. These management operations can be performed in coordination with a hypervisor that is executed by processor(s) 1110. Additionally or alternatively, the virtualization manager can perform management operations in coordination with other entities executed by processor(s) 1110 such as, for example, the compute instances themselves.

Terminology

Ordinal terms such as first, second, etc. may be used in the foregoing description and in the appended claims to describe various elements, features, acts, or operations. Unless the context clearly indicates otherwise, such elements, features, acts, or operations are not limited by those terms. The terms are used only to distinguish one element, feature, act, or operation from another. For example, a first device could be termed a second device. The first device and the second device are both devices, but they are not the same device.

Unless the context clearly indicates otherwise, as used in the foregoing description and in the appended claims, the singular forms "a," "an," and "the" are intended to include the plural forms as well.

Unless the context clearly indicates otherwise, as used in the foregoing description and in the appended claims, the terms "comprising," "including," "having," "based on," "encompassing," and other like terms, are used in the foregoing description and in the appended claims in an open-ended fashion, and do not exclude additional elements, features, acts, or operations.

Unless the context clearly indicates otherwise, the term "based on" (or similar) as used in this description or in the appended claims is an open-ended term used to describe one or more factors that affect or cause a determination or action and does not foreclose additional factors that may affect or cause a determination or action. For example, a determination or action may be affected or caused based solely on the factor(s) listed or based on the factor(s) listed and one or more additional factors.

Unless the context clearly indicates otherwise, the term "or" is used in the foregoing description and in the appended claims in its inclusive sense (and not in its exclusive sense) so that when used, for example, to connect a list of elements, features, acts, or operations, the term "or" means one, some, or all the elements, features, acts, or operations in the list.

Unless the context clearly indicates otherwise, conjunctive language in the foregoing description and in the appending claims such as the phrase "at least one of X, Y, and Z," is to be understood to convey that an item, term, etc. can be either X, Y, or Z, or a combination thereof. Thus, such conjunctive language does not require that at least one of X, at least one of Y, and at least one of Z to each be present.

What is claimed is:

1. A method comprising:

obtaining, by a provider network implemented by one or more computing devices, a set of clinical data;

detecting, by the provider network, an entity in a context of the set of clinical data;

using, by a natural language processing (NLP) pipeline implemented as NLP pipeline code executed by one or more processors of the one or more computing devices in the provider network, a machine learning-based system to determine that the entity in the context of the set of clinical data is not negated;

obtaining, by the NLP pipeline, a first negation score reflecting a probabilistic confidence of the machine learning-based system that the entity in the context is negated;

using, by the NLP pipeline, a rule-based system to determine that the entity in the context is negated;

determining, by the NLP pipeline, a continuous negation score according to a pointwise mutual information approach, the continuous negation score reflecting a probabilistic confidence of the rule-based system that the entity in the context is negated;

determining, by the NLP pipeline, an overall negation score based on the continuous negation score, the overall negation score reflecting a probabilistic confidence that the entity in the context is negated; and based on determining using the rule-based system that the entity in the context is negated, causing, by the NLP pipeline, a graphical user interface to be displayed that comprises an annotated result, the annotated result comprising an indication that the entity in the context is negated and comprising the overall negation score.

2. The method of claim 1, wherein the overall negation score is determined based on an asymmetric combination of the first negation score and the continuous negation score such that a larger of the first negation score and the continuous negation score has a greater impact on the asymmetric combination that a smaller of the first negation score and the continuous negation score.

3. The method of claim 2, wherein the asymmetric combination of the first negation score and the continuous negation score comprises a harmonic mean between the first negation score and the continuous negation score.

4. The method of claim 1, further comprising:

obtaining a second negation score reflecting a probabilistic confidence of the rule-based system that the entity in the context is negated;

determining, based on the first negation score, the overall negation score reflecting a probabilistic confidence that the entity in the context is negated; and causing a graphical user interface to be displayed that comprises the overall negation score.

5. A method comprising:

using, by a natural language processing (NLP) pipeline implemented as NLP pipeline code executed by one or more processors, a machine learning-based system to determine that an entity in a context of clinical data is not negated;

obtaining, by the NLP pipeline, a first negation score reflecting a probabilistic confidence of the machine learning-based system that the entity in the context is negated;

using, by the NLP pipeline, a rule-based system to determine that the entity in the context of clinical data is negated;

determining, by the NLP pipeline, a continuous negation score according to a pointwise mutual information approach, the continuous negation score reflecting a probabilistic confidence of the rule-based system that the entity in the context is negated;

determining, by the NLP pipeline, an overall negation score based on the continuous negation score, the overall negation score reflecting a probabilistic confidence that the entity in the context is negated; and based on determining using the rule-based system that the entity in the context is negated, storing an annotated result in a human and machine-readable data format, the annotated result comprising an indication that the entity in the context is negated and comprising the overall negation score.

6. The method of claim 5, wherein the overall negation score is determined based on an asymmetric combination of the first negation score and the continuous negation score such that a larger of the first negation score and the continuous negation score has a greater impact on the asymmetric combination that a smaller of the first negation score and the continuous negation score.

7. The method of claim 6, wherein the asymmetric combination of the first negation score and the continuous negation score comprises a harmonic mean between the first negation score and the continuous negation score.

8. The method of claim 5, wherein determining, according to the pointwise mutual information approach, the continuous negation score reflecting a probabilistic confidence of the rule-based system that the entity in the context is negated is based on determining a gold-standard negation cue that is similar to a detected negation cue in the entity in the context detected by the rule-based system, and wherein similarity between the gold-standard negation cue and the detected negation cue is measured based on a distance between a latent space embedding representing the gold-standard negation cue and a latent space embedding representing the detected negation cue.

9. The method of claim 5, further comprising determining, according to a conditional probability approach, the continuous negation score reflecting a probabilistic confidence of the rule-based system that the entity in the context is negated.

10. The method of claim 9, wherein determining, according to the conditional probability approach, the continuous negation score reflecting a probabilistic confidence of the rule-based system that the entity in the context is negated is based on determining a gold-standard negation cue that is similar to a detected negation cue in the entity in the context detected by the rule-based system, and wherein similarity between the gold-standard negation cue and the detected negation cue is measured based on a distance between a latent space embedding representing the gold-standard negation cue and a latent space embedding representing the detected negation cue.

11. The method of claim 5, further comprising causing a graphical user interface to be displayed that comprises an indication that the entity in the context is negated.

12. The method of claim 5, further comprising:

obtaining a second negation score reflecting a probabilistic confidence of the rule-based system that the entity in the context is negated;

determining, based on the first negation score, the overall negation score reflecting a probabilistic confidence that the entity in the context is negated; and causing a graphical user interface to be displayed that comprises the overall negation score.

13. A system comprising:

one or more computing devices in to implement a natural language processing (NLP) pipeline in a provider network, the natural language processing pipeline comprising instructions which when executed by one or more processors cause the NLP pipeline to perform operations comprising:

using, by the NLP pipeline, a machine learning-based system to determine that an entity in a context of clinical data is not negated;

obtaining, by the NLP pipeline, a first negation score reflecting a probabilistic confidence of the machine learning-based system that the entity in the context is negated;

using, by the NLP pipeline, a rule-based system to determine that the entity in the context of clinical data is negated;

determining, by the NLP pipeline, a continuous negation score according to a pointwise mutual information approach, the continuous negation score reflecting a probabilistic confidence of the rule-based system that the entity in the context is negated;

determining, by the NLP pipeline, an overall negation score based on the continuous negation score, the overall negation score reflecting a probabilistic confidence that the entity in the context is negated; and based on determining using the rule-based system that the entity in the context is negated, storing an annotated result in a human and machine-readable data format, the annotated result comprising an indication that the entity in the context is negated and comprising the overall negation score.

14. The system of claim 13, wherein the overall negation score is determined based on an asymmetric combination of the first negation score and the continuous negation score such that a larger of the first negation score and the continuous negation score has a greater impact on the asymmetric combination that a smaller of the first negation score and the continuous negation score.

15. The system of claim 14, wherein the asymmetric combination of the first negation score and the continuous negation score comprises a harmonic mean between the first negation score and the continuous negation score.

16. The system of claim 13, wherein determining, according to the pointwise mutual information approach, the continuous negation score reflecting a probabilistic confidence of the rule-based system that the entity in the context is negated is based on determining a gold-standard negation cue that is similar to a detected negation cue in the entity in the context detected by the rule-based system, and wherein similarity between the gold-standard negation cue and the detected negation cue is measured based on a distance between a latent space embedding representing the gold-standard negation cue and a latent space embedding representing the detected negation cue.

17. The system of claim 13, the NLP pipeline further comprising instructions which when executed by the one or more processors cause the natural language processing pipeline to perform operations comprising determining, according to a conditional probability approach, the continuous negation score reflecting a probabilistic confidence of the rule-based system that the entity in the context is negated.

18. The system of claim 17, wherein determining, according to the conditional probability approach, the continuous negation score reflecting a probabilistic confidence of the rule-based system that the entity in the context is negated is based on determining a gold-standard negation cue that is similar to a detected negation cue in the entity in the context detected by the rule-based system, and wherein similarity between the gold-standard negation cue and the detected negation cue is measured based on a distance between a latent space embedding representing the gold-standard negation cue and a latent space embedding representing the detected negation cue.

19. The system of claim 13, the NLP pipeline further comprising instructions which when executed by the one or more processors cause the natural language processing pipeline to perform operations comprising causing a graphical user interface to be displayed that comprises an indication that the entity in the context is negated.

20. The system of claim 13, the NLP pipeline further comprising instructions which when executed by the one or more processors cause the natural language processing pipeline to perform operations comprising:

obtaining a second negation score reflecting a probabilistic confidence of the rule-based system that the entity in the context is negated;

determining, based on the first negation score, the overall negation score reflecting a probabilistic confidence that the entity in the context is negated; and causing a graphical user interface to be displayed that comprises the overall negation score.

* * * * *